United States Patent
Svenstrup et al.

(10) Patent No.: US 11,370,795 B2
(45) Date of Patent: Jun. 28, 2022

(54) PROCESS FOR THE SYNTHESIS OF 6-[(3S,4S)-4-METHYL-1-(PYRIMIDIN-2-YLMETHYL)PYRROLIDIN-3-YL]-3-TETRAHYDROPYRAN-4-YL-7H-IMIDAZO[1,5-A]PYRAZIN-8-ONE

(71) Applicant: Imara Inc., Cambridge, MA (US)

(72) Inventors: Niels Svenstrup, Charlottenlund (DK); Jun Zhang, Tianjin (CN); Jikui Sun, Tianjin (CN); Yuyin Chen, Beijing (CN); Jianshe Kong, Franklin Park, NJ (US); Rujian Ma, Shanghai (CN); Junhua Zhang, Chang Zhou (CN); Liang Qin, Chang Zhou (CN); Huanming Xiao, Beijing (CN); Jinxu Sun, Beijing (CN); Xiao Meng, Shanghai (CN); Fenglai Sun, Shanghai (CN); Jingyang Zhu, Monmouth Junction, NJ (US)

(73) Assignee: Imara Inc., Cambridge, MA (US)

(*) Notice: Subject to any disclaimer, the term of this patent is extended or adjusted under 35 U.S.C. 154(b) by 0 days.

(21) Appl. No.: 16/615,347

(22) PCT Filed: May 25, 2018

(86) PCT No.: PCT/US2018/034566
§ 371 (c)(1),
(2) Date: Nov. 20, 2019

(87) PCT Pub. No.: WO2018/218104
PCT Pub. Date: Nov. 29, 2018

(65) Prior Publication Data
US 2020/0157108 A1    May 21, 2020

Related U.S. Application Data

(60) Provisional application No. 62/511,367, filed on May 26, 2017.

(51) Int. Cl.
*C07D 487/04*    (2006.01)
(52) U.S. Cl.
CPC ................. *C07D 487/04* (2013.01)
(58) Field of Classification Search
CPC .................................................. C07D 487/04
USPC ...................................................... 544/350
See application file for complete search history.

(56) References Cited

U.S. PATENT DOCUMENTS

| | | |
|---|---|---|
| 5,716,988 A | 2/1998 | Ibrahim et al. |
| 7,326,421 B2 | 2/2008 | Brekke et al. |
| 9,533,992 B2 | 1/2017 | Svenstrup et al. |
| 2008/0108697 A1 | 5/2008 | Ibrahim et al. |
| 2009/0030003 A1 | 1/2009 | Verhoest et al. |
| 2009/0220612 A1 | 9/2009 | Perera |
| 2012/0157458 A1 | 6/2012 | Ripka et al. |
| 2014/0088081 A1 | 3/2014 | Claffey et al. |
| 2014/0308336 A1 | 10/2014 | Indolfi et al. |
| 2015/0274736 A1 | 10/2015 | Svenstrup et al. |

FOREIGN PATENT DOCUMENTS

| | | |
|---|---|---|
| WO | WO-2008139293 A1 | 11/2008 |
| WO | WO-2010084438 A1 | 7/2010 |
| WO | WO-2012040230 A1 | 3/2012 |
| WO | WO-2013053690 A1 | 4/2013 |
| WO | WO-2013110768 A1 | 8/2013 |
| WO | WO-2013170069 A1 | 11/2013 |
| WO | WO-2014036555 A1 | 3/2014 |
| WO | WO-2015023557 A1 | 2/2015 |
| WO | WO-2017005786 A1 | 1/2017 |
| WO | WO-2018218104 A1 | 11/2018 |

OTHER PUBLICATIONS

Akinsheye et al.: Fetal hemoglobin in sickle cell anemia. Blood 118(1):19-27 (2011).
Almedia et al.: Hydroxyurea and a cGMP-amplifying agent have immediate benefits on acute vaso-occlusive events in sickle cell disease mice (2012) Blood 120(14):2879-2888.
Almeida et al.: High expression of the cGMP-specific phosphodiesterase, PDE9A, in sickle cell disease (SCD) and the effects of its inhibition in erythroid cells and SCD neutrophils. British Journal of Haematology 142(5):836-44 (2008).
Alsultan et al.: Genetic studies of fetal hemoglobin in the Arab-Indian haplotype sickle cell-β(o) thalassemia. American Journal of Hematology 88(6):531-532 (2013).
Berge et al.: (1977) Pharmaceuticals Salts, J. Pharma. Sci. 66: 1-19.
Miguel et al.: Inhibition of phosphodiesterase 9A reduces cytokine-stimulated in vitro adhesion of neutrophils from sickle cell anemia individuals. Inflammation Research 60(7):633-42 (2011).
PCT/US2018/034566 International Search Report and Written Opinion dated Aug. 21, 2018.
PubChem CID 71550282 https://pubchem.ncbi.nlm.nih.gov/compound/71550282 (2013).

*Primary Examiner* — Douglas M Willis
(74) *Attorney, Agent, or Firm* — Wilson Sonsini Goodrich & Rosati

(57) ABSTRACT

The present invention relates a process for the synthesis of 6-((3S,4S)-4-methyl-1-(pyrimidin-2 ylmethyl)pyrrolidin-3-yl)-3-tetrahydropyran-4-yl-7H-imidazo[1,5-a]pyrazin-8-one, comprising use of the chiral acid (+)-O,O-Dibenzoyl-D-tartaic acid.

9 Claims, No Drawings

PROCESS FOR THE SYNTHESIS OF 6-[(3S,4S)-4-METHYL-1-(PYRIMIDIN-2-YLMETHYL)PYRROLIDIN-3-YL]-3-TETRAHYDROPYRAN-4-YL-7H-IMIDAZO[1,5-A]PYRAZIN-8-ONE

REFERENCE TO RELATED APPLICATIONS

The present application claims priority to U.S. Provisional Application No. 62/511,367 filed May 26, 2017, entitled Methods of Making and Using PDE9 Inhibitors, the contents of which are incorporated herein by reference in its entirety.

FIELD OF THE DISCLOSURE

The present invention relates to cyclic guanylate monophosphate (cGMP)-specific phosphodiesterase type 9 inhibitors (hereinafter referred to as PDE9 inhibitors).

BACKGROUND

Phosphodiesterases (PDEs) are a family of enzymes degrading cyclic nucleotides and thereby regulating the cellular levels of second messengers throughout the entire body. PDEs represent attractive drug targets, as proven by a number of compounds that have been introduced to clinical testing and the market, respectively. PDEs are encoded by 21 genes that are functionally separated into 11 families differing with respect to kinetic properties, substrate selectivity, expression, localization pattern, activation, regulation factors and inhibitor sensitivity. The function of PDEs is the degradation of the cyclic nucleotide monophosphates cyclic Adenosine Monophosphate (cAMP) and/or Guanosine Monophosphate (cGMP), which are important intracellular mediators involved in numerous vital processes including the control of neurotransmission and smooth muscle contraction and relaxation.

PDE9 is cGMP specific (Km for cAMP is >1000-fold higher than Km for cGMP) and is hypothesized to be a key player in regulating cGMP levels as it has the lowest Km among the PDEs for this nucleotide. PDE9 is expressed throughout the brain at low levels with the potential for regulating basal cGMP.

WO 2012/040230 discloses PDE9 inhibitors with imidazotriazinone backbone for the use as a medicament in the treatment of PDE9 associated diseases, including CNS and neurodegenerative disorders.

WO 2008/139293 and WO 2010/084438 both disclose amino-heterocyclic compounds that are PDE9 inhibitors and their use in treating neurodegenerative and cognitive disorders.

In the periphery, PDE9 expression is highest in prostate, intestine, kidney and haematopoietic cells, enabling therapeutic potential in various non-CNS indications.

SUMMARY

The present invention provides methods of making and using PDE9 inhibitors that have been shown to have a low blood brain barrier penetration and thus may be particularly useful for the treatment of peripheral diseases such as benign prostate hyperplasia (BPH), urinary tract dysfunctional epithelium disease, erectile dysfunction, type 2 diabetes and sickle cell disease (SCD). Further, the PDE9 inhibitors of the present invention are significantly stronger PDE9 inhibitors than PDE1 inhibitors. This PDE inhibition selectivity is important as PDE1 is expressed in heart and testes and inhibition of these PDE1 isoforms is thought to be a potential cause of cardiovascular and reproductive side effects.

DETAILED DESCRIPTION

I. Compounds of the Invention

One aspect of the present invention provides a PDE9-inhibiting compound or a PDE9 inhibitor that may be used to treat sickle cell disease (SCD). The PDE9 inhibitors of the present invention have been shown to have a low blood brain barrier penetration and thus may be particularly useful for the treatment of peripheral diseases such as benign prostate hyperplasia (BPH), urinary tract dysfunctional epithelium disease, erectile dysfunction, type 2 diabetes and sickle cell disease (SCD). Further, the PDE9 inhibitors of the present invention are significantly stronger PDE9 inhibitors than PDE1 inhibitors. This PDE inhibition selectivity is important as PDE1 is expressed in heart and testes and inhibition of these PDE1 isoforms is thought to be a potential cause of cardiovascular and reproductive side effects.

PDE9 Inhibitors

In the context of the present invention a compound is considered to be a PDE9 inhibitor if the amount required to reach the $IC_{50}$ level of any of the three PDE9 isoforms is 10 micromolar or less, preferably less than 9 micromolar, such as 8 micromolar or less, such as 7 micromolar or less, such as 6 micromolar or less, such as 5 micromolar or less, such as 4 micromolar or less, such as 3 micromolar or less, more preferably 2 micromolar or less, such as 1 micromolar or less, in particular 500 nM or less. In preferred embodiments the required amount of PDE9 inhibitor required to reach the $IC_{50}$ level of PDE9 is 400 nM or less, such as 300 nM or less, 200 nM or less, 100 nM or less, or even 80 nM or less, such as 50 nM or less, for example 25 nM or less.

Throughout this application the notations $IC_{50}$ and $IC_{50}$ are used interchangeably.

In some embodiments, the PDE9 inhibitor of the present invention has low or no blood brain barrier penetration. For example, the ratio of the concentration of a PDE9 inhibitor of the present invention in the brain to the concentration of it in the plasma (brain/plasma ratio) may be less than about 0.50, about 0.40, about 0.30, about 0.20, about 0.10, about 0.05, about 0.04, about 0.03, about 0.02, or about 0.01. The brain/plasma ratio may be measured 30 min or 120 min after administration of the PDE9 inhibitor.

Isomeric Forms

Where compounds of the present invention contain one or more chiral centers reference to any of the compounds will, unless otherwise specified, cover the enantiomerically or diastereomerically pure compound as well as mixtures of the enantiomers or diastereomers in any ratio.

In one embodiment, the PDE9 inhibiting compounds of the present invention that are used to treat sickle cell disease comprise an imidazopyrazinone backbone. They may have structure (I) (also referred to as compounds of formula (I))

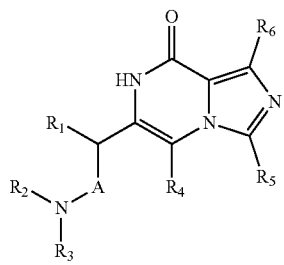

(I)

wherein R2 is cyclized with either R1 or R3,
wherein R1, R2 and R3 are
R1, when cyclized with R2, is

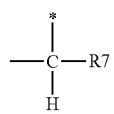

wherein R7 is selected from the group consisting of H, —CH$_3$, —C$_2$H$_5$, and —C$_3$H$_7$,
wherein * denotes the cyclization point, and
R1, when not cyclized, is selected from the group consisting of
H and

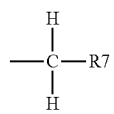

wherein R7 is selected from the group consisting of H, —CH$_3$, —C$_2$H$_5$, and —C$_3$H$_7$
R2 is a compound selected from the group consisting of

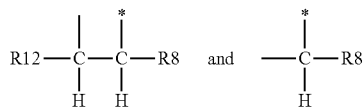

wherein R8 and R12 independently are selected from the group consisting of H, —CH$_3$, —C$_2$H$_5$, and —C$_3$H$_7$
wherein * denotes the cyclization point, and
R3, when cyclized with R2, is

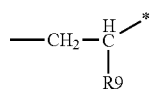

wherein * denotes the cyclization point, and
wherein R9 is selected from the group consisting of H, C$_1$-C$_6$ alkyl, substituted C$_1$-C$_6$ alkyl, branched C$_3$-C$_6$ alkyl, C$_3$-C$_6$ cycloalkyl, substituted C$_3$-C$_6$ cycloalkyl, C$_6$-C$_{10}$ aryl, substituted C$_6$-C$_{10}$ aryl, C$_3$-C$_9$ heteroaryl, substituted C$_3$-C$_9$ heteroaryl, C$_1$-C$_6$ alkoxy, substituted C$_1$-C$_6$ alkoxy, branched C$_3$-C$_6$ alkoxy, C$_3$-C$_6$ cycloalkoxy, substituted C$_3$-C$_6$ cycloalkoxy, C$_6$-C$_{10}$ aryloxy, substituted C$_6$-C$_{10}$ aryloxy, C$_3$-C$_9$ heteroaryloxy, substituted C$_3$-C$_9$ heteroaryloxy; and R3, when not cyclized, is

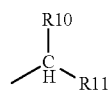

wherein
R10 is selected from the group consisting of H, —CH$_3$, and —C$_2$H$_5$; and
R11 is selected from the group consisting of C$_6$-C$_{10}$ aryl, substituted C$_6$-C$_{10}$ aryl, C$_3$-C$_9$ heteroaryl, substituted C$_3$-C$_9$ heteroaryl;
R4 is selected from the group consisting of hydrogen, —CH$_3$, —C$_2$H$_5$, —C$_3$H$_7$, —CF$_3$, —CN, F and Cl;
R5 is selected from the group consisting of C$_6$-C$_{10}$ aryl, substituted C$_6$-C$_{10}$ aryl, C$_3$-C$_9$ heteroaryl, substituted C$_3$-C$_9$ heteroaryl, C$_3$-C$_6$ heterocyclyl, substituted C$_3$-C$_6$ heterocyclyl, C$_3$-C$_6$ cycloalkyl, and substituted C$_3$-C$_6$ cycloalkyl;
R6 is selected from the group consisting of hydrogen, F, Cl, CN, —CH$_3$, —C$_2$H$_5$, —C$_3$H$_7$, and —CF$_3$;
A is absent or —CH$_2$—;
and tautomers and pharmaceutically acceptable acid addition salts thereof, and polymorphic forms thereof.

Non-limiting examples of PDE9-inhibiting compounds of formula (I) are disclosed in WO 2013/053690, the contents of which are incorporated herein by reference in their entirety.

For example, the PDE9 inhibitor with an imidazopyrazinone backbone may be selected from the group consisting of:

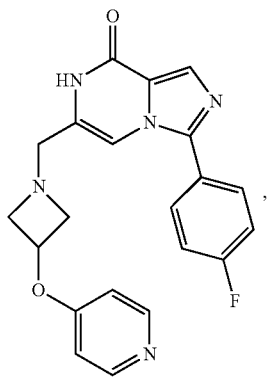

(compound P1)

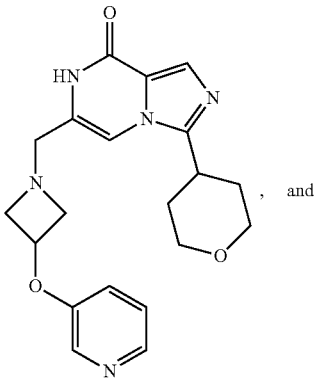

(compound P2)

and (compound P3)

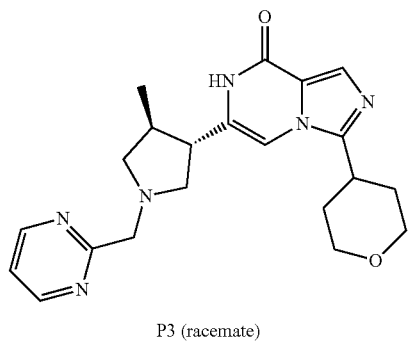

P3 (racemate)

in racemic form and in enantiomerically enriched or pure form.

In another embodiment, the PDE9 inhibiting compounds of the present invention that are used to treat sickle cell disease comprise an imidazotriazinone backbone. They may have structure (II) (also referred to as compounds of formula (II))

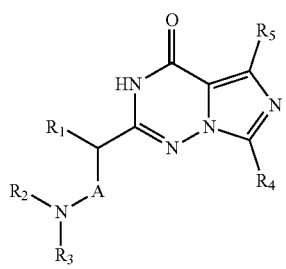
(II)

wherein R2 is cyclized with either R1 or R3, wherein R1, R2 and R3 are

R1, when cyclized with R2, is

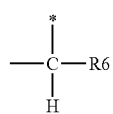

wherein R6 is selected from the group consisting of H, —CH$_3$, —C$_2$H$_5$, and —C$_3$H$_7$, wherein * denotes the cyclization point, and R1, when not cyclized, is selected from the group consisting of H and

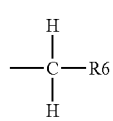

wherein R6 is selected from the group consisting of H, —CH$_3$, —C$_2$H$_5$, and —C$_3$H$_7$ R2 is a compound selected from the group consisting of

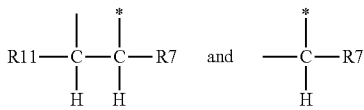

wherein R7 and R11 independently are selected from the group consisting of H, —CH$_3$, —C$_2$H$_5$, and —C$_3$H$_7$ wherein * denotes the cyclization point, and R3, when cyclized with R2, is

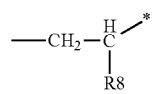

wherein * denotes the cyclization point, and wherein R8 is selected from the group consisting of H, C$_1$-C$_6$ alkyl, substituted C$_1$-C$_6$ alkyl, branched C$_3$-C$_6$ alkyl, C$_3$-C$_6$ cycloalkyl, substituted C$_3$-C$_6$ cycloalkyl, C$_6$-C$_{10}$ aryl, substituted C$_6$-C$_{10}$ aryl, C$_3$-C$_9$ heteroaryl, substituted C$_3$-C$_9$ heteroaryl, C$_1$-C$_6$ alkoxy, substituted C$_1$-C$_6$ alkoxy, branched C$_3$-C$_6$ alkoxy, C$_3$-C$_6$ cycloalkoxy, substituted C$_3$-C$_6$ cycloalkoxy, C$_6$-C$_{10}$ aryloxy, substituted C$_6$-C$_{10}$ aryloxy, C$_3$-C$_9$ heteroaryloxy, substituted C$_3$-C$_9$ heteroaryloxy; and R3, when not cyclized, is

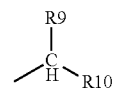

wherein

R9 is selected from the group consisting of H, —CH$_3$, and —C$_2$H$_5$; and

R10 is selected from the group consisting of C$_6$-C$_{10}$ aryl, substituted C$_6$-C$_{10}$ aryl, C$_3$-C$_9$ heteroaryl, substituted C$_3$-C$_9$ heteroaryl R4 is selected from the group consisting of C$_6$-C$_{10}$ aryl, substituted C$_6$-C$_{10}$ aryl, C$_3$-C$_9$ heteroaryl, substituted C$_3$-C$_9$ heteroaryl, C$_3$-C$_6$ heterocyclyl, substituted C$_3$-C$_6$ heterocyclyl, C$_3$-C$_6$ cycloalkyl, and substituted C$_3$-C$_6$ cycloalkyl;

R5 is selected from the group consisting of hydrogen, F, Cl, CN, —C$_2$H$_5$, —C$_3$H$_7$, and —CF$_3$;

A is absent or —CH$_2$—, and tautomers and pharmaceutically acceptable acid addition salts thereof, and polymorphic forms thereof.

Non-limiting examples of PDE9 inhibitors of formula (II) are disclosed in WO 2013/110768, the contents of which are incorporated herein by reference in their entirety.

For example, the PDE9 inhibitor with an imidazotriazinone backbone may be (compound P4)

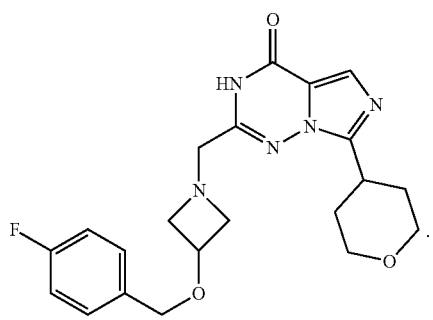

P4

Non-Limiting Embodiments of the Invention

Table 1 lists compound examples of the invention and the corresponding IC$_{50}$ values (nM) determined. Further, the concentration of compounds in plasma and brain, determined as described in the section "Blood Brain Barrier penetration", are listed. Each of the compounds constitutes an individual embodiment of the present invention:

II. Pharmaceutical Composition

The present invention further provides a pharmaceutical composition comprising a therapeutically effective amount of any of the compounds of the present invention and a pharmaceutically acceptable carrier or diluent. The present invention also provides a pharmaceutical composition comprising a therapeutically effective amount of one of the specific compounds disclosed herein and a pharmaceutically acceptable carrier or diluent.

Pharmaceutically Acceptable Salts

The present invention also comprises salts of the compounds, typically, pharmaceutically acceptable salts. Such salts include pharmaceutically acceptable acid addition salts. Acid addition salts include salts of inorganic acids as well as organic acids.

Representative examples of suitable inorganic acids include hydrochloric, hydrobromic, hydroiodic, phosphoric, sulfuric, sulfamic, nitric acids and the like. Representative examples of suitable organic acids include formic, acetic, trichloroacetic, trifluoroacetic, propionic, benzoic, cinnamic, citric, fumaric, glycolic, itaconic, lactic, methanesulfonic, maleic, malic, malonic, mandelic, oxalic, picric, pyruvic, salicylic, succinic, methane sulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, theophylline ace-

TABLE 1

Compound examples of the invention, IC50 values and plasma/brain concentration

| Compound | PDE9 IC50 (nM) | PDE1 IC50 (nM) | Plasma concentration after 30 minutes and 120 minutes (ng/mL) | Brain concentration after 30 minutes and 120 minutes (ng/mL) | Brain/Plasma ratio after 30 minutes and 120 minutes |
|---|---|---|---|---|---|
| Compound (P1) | 42 | 45090 | 30 min.: 719<br>120 min.: 86 | 30 min.: 42<br>120 min.: 7 | 0.06<br>0.08 |
| Compound (P2) | 36 | 5283 | 30 min.: 715<br>120 min.: 11 | Below detection limit | Not calculated (brain concentration below limit of detection) |
| Compound (P3, enantiomer 1, i.e., P3.1) | 10 | 3000 | 30 min.: 1620<br>120 min.: 226 | 30 min.: 67<br>120 min.: 7 | 0.04<br>0.03 |
| Compound (P4) | 10 | 1009 | 30 min.: 3380<br>120 min.: 352 | 30 min.: 125<br>120 min.: 15 | 0.04<br>0.04 |
| 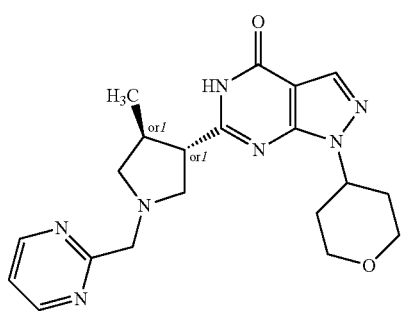Reference compound disclosed in WO2008/139293 (AF27873 or PF-04447943) | 70 | 2500 | 30 min.: 1230<br>120 min.: 529 | 30 min.: 500<br>120 min.: 215 | 0.41<br>0.41 | tic acids, as well as the 8-halotheophyllines, for example 8-bromotheophylline and the like. Further examples of pharmaceutically acceptable inorganic or organic acid addition salts include the pharmaceutically acceptable salts listed in Berge, S. M. et al., J. Pharm. Sci. 1977, 66, 2, the contents of which are hereby incorporated by reference.

Furthermore, the compounds of this invention may exist in unsolvated as well as in solvated forms with pharmaceutically acceptable solvents such as water, ethanol and the like. In general, the solvated forms are considered equivalent to the unsolvated forms for the purposes of this invention.

The compounds of the invention may be administered alone or in combination with pharmaceutically acceptable carriers, diluents or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 22nd Edition, Gennaro, Ed., Mack Publishing Co., Easton, Pa., 2013.

The pharmaceutical compositions may be specifically formulated for administration by any suitable route such as oral, rectal, nasal, pulmonary, topical (including buccal and sublingual), transdermal, intracisternal, intraperitoneal, vaginal and parenteral (including subcutaneous, intramuscular, intrathecal, intravenous and intradermal) routes. It will be appreciated that the route will depend on the general health and age of the subject to be treated, the nature of the condition to be treated and the active ingredient.

Pharmaceutical compositions for oral administration include solid dosage forms such as capsules, tablets, dragees, pills, lozenges, powders and granules. Where appropriate, the compositions may be prepared with coatings such as enteric coatings or they may be formulated so as to provide controlled release of the active ingredient such as sustained or prolonged release according to methods well known in the art. Liquid dosage forms for oral administration include solutions, emulsions, suspensions, syrups and elixirs.

Pharmaceutical compositions for parenteral administration include sterile aqueous and nonaqueous injectable solutions, dispersions, suspensions or emulsions as well as sterile powders to be reconstituted in sterile injectable solutions or dispersions prior to use. Other suitable administration forms include, but are not limited to, suppositories, sprays, ointments, creams, gels, inhalants, dermal patches and implants.

Typical oral dosages range from about 0.001 to about 100 mg/kg body weight per day. Typical oral dosages also range from about 0.01 to about 50 mg/kg body weight per day. Typical oral dosages further range from about 0.05 to about 10 mg/kg body weight per day. Oral dosages are usually administered in one or more dosages, typically, one to three dosages per day. The exact dosage will depend upon the frequency and mode of administration, the gender, age, weight and general health of the subject treated, the nature and severity of the condition treated and any concomitant diseases to be treated and other factors evident to those skilled in the art.

The formulations may also be presented in a unit dosage form by methods known to those skilled in the art. For illustrative purposes, a typical unit dosage form for oral administration may contain from about 0.01 to about 1000 mg, from about 0.05 to about 500 mg, or from about 0.5 mg to about 200 mg.

For parenteral routes such as intravenous, intrathecal, intramuscular and similar administration, typical doses are on the order of half the dose employed for oral administration.

The present invention also provides a process for making a pharmaceutical composition comprising admixing a therapeutically effective amount of a compound of the present invention and at least one pharmaceutically acceptable carrier or diluent. In an embodiment, of the present invention, the compound utilized in the aforementioned process is one of the specific compounds disclosed in the Experimental Section herein.

The compounds of this invention are generally utilized as the free substance or as a pharmaceutically acceptable salt thereof. Such salts are prepared in a conventional manner by treating a solution or suspension of a compound of the present invention with a molar equivalent of a pharmaceutically acceptable acid. Representative examples of suitable organic and inorganic acids are described above.

For parenteral administration, solutions of the compounds of the present invention in sterile aqueous solution, aqueous propylene glycol, aqueous vitamin E or sesame or peanut oil may be employed. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The compounds of the present invention may be readily incorporated into known sterile aqueous media using standard techniques known to those skilled in the art.

Suitable pharmaceutical carriers include inert solid diluents or fillers, sterile aqueous solutions and various organic solvents. Examples of solid carriers include lactose, terra alba, sucrose, cyclodextrin, talc, gelatin, agar, pectin, acacia, magnesium stearate, stearic acid and lower alkyl ethers of cellulose. Examples of liquid carriers include, but are not limited to, syrup, peanut oil, olive oil, phospholipids, fatty acids, fatty acid amines, polyoxyethylene and water. Similarly, the carrier or diluent may include any sustained release material known in the art, such as glyceryl monostearate or glyceryl distearate, alone or mixed with a wax. The pharmaceutical compositions formed by combining the compounds of the present invention and a pharmaceutically acceptable carrier are then readily administered in a variety of dosage forms suitable for the disclosed routes of administration. The formulations may conveniently be presented in unit dosage form by methods known in the art of pharmacy.

Formulations of the present invention suitable for oral administration may be presented as discrete units such as capsules or tablets, each containing a predetermined amount of the active ingredient, and optionally a suitable excipient. Furthermore, the orally available formulations may be in the form of a powder or granules, a solution or suspension in an aqueous or non-aqueous liquid, or an oil-in-water or water-in-oil liquid emulsion.

If a solid carrier is used for oral administration, the preparation may be tabletted, placed in a hard gelatine capsule in powder or pellet form or it may be in the form of a troche or lozenge. The amount of solid carrier will vary widely but will range from about 25 mg to about 1 g per dosage unit. If a liquid carrier is used, the preparation may be in the form of a syrup, emulsion, soft gelatine capsule or sterile injectable liquid such as an aqueous or non-aqueous liquid suspension or solution.

The pharmaceutical compositions of the invention may be prepared by conventional methods in the art. For example, tablets may be prepared by mixing the active ingredient with ordinary adjuvants and/or diluents and subsequently compressing the mixture in a conventional tabletting machine prepare tablets. Examples of adjuvants or diluents comprise: corn starch, potato starch, talcum, magnesium stearate, gelatin, lactose, gums, and the like. Any other adjuvants or additives usually used for such purposes such as colorings, flavorings, preservatives etc. may be used provided that they are compatible with the active ingredients.

The pharmaceutical compositions may comprise at least 10%, 20%, 30%, 40%, 50%, 60%, 70%, 80%, or 90% by weight of PDE9 inhibitors of the present invention.

In one embodiment, the pharmaceutical composition comprising compounds of the present invention is used in combination with an additional active agent, such as HU.

III. Methods of Using Compounds of the Invention

PDE9 is expressed specifically in the human haematopoietic system including neutrophils, reticulocytes erythroid and erythroleukaemic cells. Furthermore, sickle cell disease (SCD) patients exhibit a marked and significant elevation of PDE9 expression in reticulocytes and neutrophils compared to healthy individuals (Almeida et al., Br J Haematol. 2008 September; 142(5):836-44). Evidence additionally demonstrates a link between PDE9 and cell adhesion since pharmacologic PDE9 inhibition ameliorates the increased adhesive properties of SCD neutrophils (Miguel et al., Inflamm Res. 2011 July; 60(7):633-42). The mechanism by which PDE9 inhibition decreases cell adhesion has been shown to be mediated by increased cGMP and decreased endothelial adhesion molecule expression. Importantly, in an animal model of SCD, the PDE9 inhibitor-mediated decrease in cell adhesion had the functional effect of increased cell survival. In addition to demonstrating decreased cell adhesion comparable to hydroxyurea (HU), PDE9 inhibition resulted in increased fetal non-sickled haemoglobin (HbF) production, which reduced the cellular concentration of abnormal haemoglobin (HbS) within red blood cells (RBCs) resulting in less polymerization of the abnormal haemoglobin and its associated sequelae. The importance of increasing HbF in treating SCD is evidenced by results of large studies like the Cooperative Study of Sickle Cell Disease, as well as studies in a variety of patient cohorts outside of the US, showing that HbF is among the most important modifiers of this disease (Alsultan et al., *Am J Hematol.*, 88(6):531-2 (2013)) as well as data showing that modifiers of HbF improve other hematological parameters (Akinsheye, *Blood,* 118(1):19-27 (2011)). Finally, Almeida and colleagues demonstrated that treatment with HU combined with PDE9 inhibition in a mouse model of SCD leads to an additional beneficial amplification of the cGMP elevating effects of HU (Almeida et al., Blood. 2012 Oct. 4; 120(14):2879-88). In conclusion, PDE9 inhibition can modulate both the expression of fetal haemoglobin production as well as decrease cell adhesion, both mechanisms key for the treatment of SCD.

One aspect of the present invention provides methods of using PDE9 inhibitors of the present invention and pharmaceutical compositions comprising PDE9 inhibitors of the present invention.

PDE9 inhibitors of the present invention may be used to treat sickle cell disease or any disease and/or symptom related to sickle cell disease, such as anemia, sickle-hemoglobin C disease (SC), beta thalassemia (beta-plus thalassemia and beta-zero thalassemia), vaso-occlusive crisis, attacks of pain (sickle cell crisis), splenic sequestration crisis, acute chest syndrome, aplastic crisis, haemolytic crisis, long-term pain, bacterial infections, and stroke.

In one embodiment, PDE9 inhibitors of the present invention are used to treat beta thalassemia of a subject and/or to increase hemoglobin levels in the subject.

In another embodiment, PDE9 inhibitors of the present invention are used to increase cGMP levels in a cell or in the plasma of a subject, wherein the subject has sickle cell disease. The cell may be, but not limited to, red blood cells and/or white blood cells. The cGMP level may be increased by at least 50%, 100%, 150%, 2 times, 3 times, 4 times, 5 times, 10 times, 15 times, 20 times, or 25 times.

In another embodiment, PDE9 inhibitors of the present invention are used to increase fetal haemoglobin (HbF) positive red blood cell number in a subject, wherein the subject has sickle cell disease. The HbF positive red blood cell number is increased by at least 50%, 100%, 150%, 2 times, 3 times, 4 times, 5 times, 10 times, 15 times, 20 times, or 25 times.

In another embodiment, PDE9 inhibitors of the present invention are used to reduce sickle red blood cell percentage (% sickle RBC), stasis percentage (% stasis), total bilirubin, or total leucocyte count in a subject, wherein the subject has sickle cell disease. The % sickle RBC, % stasis, total bilirubin, total leucocyte count or spleen weight is decreased by at least 10%, 20%, 30%, 40%, 50%, 60% or 70%.

cGMP level may be measured with any suitable method in the art, such as enzyme immunoassay.

HbF positive cells, as used herein, means red blood cells with HbF. HbF positive cells may be measured from a blood sample with any suitable method in the art, such as electrophoresis and/or colorimetric methods.

Sickle red blood cells, sickled red blood cells, as used herein, means red blood cells with a crescent or sickle shape. % sickle red blood cell may be measured from a blood sample with any suitable method in the art.

Stasis or microvascular stasis, as used herein, is serious slowing, or complete cessation, of blood or lymph flow through vessels. % stasis is the number of static (no flow) venules divided by the number of flowing venules times 100. % stasis may be measured with any suitable method in the art.

Total bilirubin, as used herein, means both unconjugated and conjugated bilirubin. Total bilirubin levels may be measured from a blood sample with any suitable method in the art.

Total leucocyte count or total white blood cell count, as used herein, is a blood test that measures the number of white blood cells in the body. It may be measured from a blood sample with any suitable method in the art.

Another aspect of the present invention provides methods of using a PDE9 inhibitor of the present invention in combination with at least one other active agent. They may be administered simultaneously or sequentially. They may be present as a mixture for simultaneous administration, or may each be present in separate containers for sequential administration.

The term "simultaneous administration", as used herein, is not specifically restricted and means that the PDE9 inhibitor of the present invention and the at least one other active agent are substantially administered at the same time, e.g. as a mixture or in immediate subsequent sequence.

The term "sequential administration", as used herein, is not specifically restricted and means that the PDE9 inhibitor of the present invention and the at least one other active agent are not administered at the same time but one after the other, or in groups, with a specific time interval between administrations. The time interval may be the same or different between the respective administrations of PDE9 inhibitor of the present invention and the at least one other active agent and may be selected, for example, from the range of 2 minutes to 96 hours, 1 to 7 days or one, two or three weeks. Generally, the time interval between the administrations may be in the range of a few minutes to hours, such as in the range of 2 minutes to 72 hours, 30 minutes to 24 hours, or 1 to 12 hours. Further examples include time intervals in the range of 24 to 96 hours, 12 to 36 hours, 8 to 24 hours, and 6 to 12 hours.

The molar ratio of the PDE9 inhibitor of the present invention and the at least one other active agent is not particularly restricted. For example, when a PDE9 inhibitor of the present invention and one other active agent are combined in a composition, the molar ratio of them may be in the range of 1:500 to 500:1, or of 1:100 to 100:1, or of 1:50 to 50:1, or of 1:20 to 20:1, or of 1:5 to 5:1, or 1:1. Similar molar ratios apply when a PDE9 inhibitor of the present invention and two or more other active agent are combined in a composition. The PDE9 inhibitor of the present invention may comprise a predetermined molar weight percentage from about 1% to 10%, or about 10% to about 20%, or about 20% to about 30%, or about 30% to 40%, or about 40% to 50%, or about 50% to 60%, or about 60% to 70%, or about 70% to 80%, or about 80% to 90%, or about 90% to 99% of the composition.

The other active agent may be a different PDE9 inhibitor of the present invention or HU. The other active agent may also be an antibiotic agent such as penicillin, a nonsteroidal anti-inflammatory drug (NSAIDS) such as diclofenac or naproxen, a pain relief medication such as opioid, or folic acid.

Yet another aspect of the present invention provides methods of using a PDE9 inhibitor of the present invention in combination with at least one other therapy, such as but not limited to blood transfusion, bone marrow transplant, or gene therapy.

IV. Kits and Devices

The invention provides a variety of kits and devices for conveniently and/or effectively carrying out methods of the present invention. Typically kits will comprise sufficient amounts and/or numbers of components to allow a user to perform multiple treatments of a subject(s) and/or to perform multiple experiments.

In one embodiment, the present invention provides kits for treating sickle cell disease, comprising a PDE9 inhibitor compound of the present invention or a combination of PDE9 inhibitor compounds of the present invention, optionally in combination with any other active agents, such as HU, an antibiotic agent such as penicillin, a nonsteroidal anti-inflammatory drug (NSAIDS) such as diclofenac or naproxen, a pain relief medication such as opioid, or folic acid.

The kit may further comprise packaging and instructions and/or a delivery agent to form a formulation composition. The delivery agent may comprise a saline, a buffered solution, or any delivery agent disclosed herein. The amount of each component may be varied to enable consistent, reproducible higher concentration saline or simple buffer formulations. The components may also be varied in order to increase the stability of PDE9 inhibitor compounds in the buffer solution over a period of time and/or under a variety of conditions.

The present invention provides for devices that may incorporate PDE9 inhibitor compounds of the present invention. These devices contain in a stable formulation available to be immediately delivered to a subject in need thereof, such as a human patient with sickle cell disease or beta thalassemia.

Non-limiting examples of the devices include a pump, a catheter, a needle, a transdermal patch, a pressurized olfactory delivery device, iontophoresis devices, multi-layered microfluidic devices. The devices may be employed to deliver PDE9 inhibitor compounds of the present invention according to single, multi- or split-dosing regiments. The devices may be employed to deliver PDE9 inhibitor compounds of the present invention across biological tissue, intradermal, subcutaneously, or intramuscularly. More examples of devices suitable for delivering PDE9 inhibitor compounds include but not limited to a medical device for intravesical drug delivery disclosed in International Publication WO 2014036555, a glass bottle made of type I glass disclosed in US Publication No. 20080108697, a drug-eluting device comprising a film made of a degradable polymer and an active agent as disclosed in US Publication No. 20140308336, an infusion device having an injection micropump, or a container containing a pharmaceutically stable preparation of an active agent as disclosed in U.S. Pat. No. 5,716,988, an implantable device comprising a reservoir and a channeled member in fluid communication with the reservoir as disclosed in International Publication WO 2015023557, a hollow-fibre-based biocompatible drug delivery device with one or more layers as disclosed in US Publication No. 20090220612, an implantable device for drug delivery including an elongated, flexible device having a housing defining a reservoir that contains a drug in solid or semi-solid form as disclosed in International Publication WO 2013170069, a bioresorbable implant device disclosed in U.S. Pat. No. 7,326,421, contents of each of which are incorporated herein by reference in their entirety.

V. Definitions

The articles "a" and "an," as used herein, should be understood to mean "at least one," unless clearly indicated to the contrary.

The phrase "and/or," as used herein, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements).

As used herein, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of"

or "exactly one of," or, when used in the claims, "consisting of," will refer to the inclusion of exactly one element of a number or list of elements.

In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein, the phrase "at least one" in reference to a list of one or more elements should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

As used herein, all transitional phrases such as "comprising," "including," "carrying," "having," "containing," "involving," "holding," and the like are to be understood to be open-ended, i.e., to mean including but not limited to.

Only the transitional phrases "consisting of" and "consisting essentially of" shall be closed or semi-closed transitional phrases, respectively, as set forth in the United States Patent Office Manual of Patent Examining Procedures.

As used herein, a "subject" or a "patient" refers to any mammal (e.g., a human), such as a mammal that may be susceptible to a disease or disorder, for example, tumorigenesis or cancer. Examples include a human, a non-human primate, a cow, a horse, a pig, a sheep, a goat, a dog, a cat, or a rodent such as a mouse, a rat, a hamster, or a guinea pig. In various embodiments, a subject refers to one that has been or will be the object of treatment, observation, or experiment. For example, a subject can be a subject diagnosed with cancer or otherwise known to have cancer or one selected for treatment, observation, or experiment on the basis of a known cancer in the subject.

As used herein, "treatment" or "treating" refers to amelioration of a disease or disorder, or at least one sign or symptom thereof. "Treatment" or "treating" can refer to reducing the progression of a disease or disorder, as determined by, e.g., stabilization of at least one sign or symptom or a reduction in the rate of progression as determined by a reduction in the rate of progression of at least one sign or symptom. In another embodiment, "treatment" or "treating" refers to delaying the onset of a disease or disorder.

As used herein, "prevention" or "preventing" refers to a reduction of the risk of acquiring or having a sign or symptom a given disease or disorder, i.e., prophylactic treatment.

The phrase "therapeutically effective amount" as used herein means that amount of a compound, material, or composition comprising a compound of the present teachings that is effective for producing a desired therapeutic effect. Accordingly, a therapeutically effective amount treats or prevents a disease or a disorder, e.g., ameliorates at least one sign or symptom of the disorder. In various embodiments, the disease or disorder is a cancer.

A dash ("—") that is not between two letters or symbols is used to indicate a point of attachment for a substituent. For example, —$CONH_2$ is attached through the carbon atom (C).

By "optional" or "optionally," it is meant that the subsequently described event or circumstance may or may not occur, and that the description includes instances where the event or circumstance occurs and instances in which it does not. For example, "optionally substituted aryl" encompasses both "aryl" and "substituted aryl" as defined herein. It will be understood by those ordinarily skilled in the art, with respect to any group containing one or more substituents, that such groups are not intended to introduce any substitution or substitution patterns that are sterically impractical, synthetically non-feasible, and/or inherently unstable.

The term "alkyl" as used herein refers to a saturated straight or branched hydrocarbon, such as a straight or branched group of 1-22, 1-8, 1-6, or 1-4 carbon atoms, referred to herein as $(C_1$-$C_{22})$alkyl, $(C_1$-$C_8)$alkyl, $(C_1$-$C_6)$alkyl, and $(C_1$-$C_4)$alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, and octyl.

The term "alkenyl" as used herein refers to an unsaturated straight or branched hydrocarbon having at least one carbon-carbon double bond (shown, for example, as "="), such as a straight or branched group of 2-22, 2-8, 2-6, or 2-4 carbon atoms, referred to herein as $(C_2$-$C_{22})$alkenyl, $(C_2$-$C_8)$alkenyl, $(C_2$-$C_6)$alkenyl, and $(C_2$-$C_4)$alkenyl, respectively. Exemplary alkenyl groups include, but are not limited to, vinyl, allyl, butenyl, pentenyl, hexenyl, butadienyl, pentadienyl, hexadienyl, 2-ethylhexenyl, 2-propyl-2-butenyl, and 4-(2-methyl-3-butene)-pentenyl.

The term "alkynyl" as used herein refers to an unsaturated straight or branched hydrocarbon having at least one carbon-carbon triple bond (shown, for example, as "≡") such as a straight or branched group of 2-22, 2-8, 2-6, 2-4 carbon atoms, referred to herein as $(C_2$-$C_{22})$alkynyl, $(C_2$-$C_8)$alkynyl, $(C_2$-$C_6)$alkynyl, and $(C_2$-$C_4)$alkynyl, respectively. Exemplary alkynyl groups include, but are not limited to, ethynyl, propynyl, butynyl, pentynyl, hexynyl, methylpropynyl, 4-methyl-1-butynyl, 4-propyl-2-pentynyl, and 4-butyl-2-hexynyl.

The term "cycloalkyl" as used herein refers to a saturated or unsaturated monocyclic, bicyclic, other multicyclic, or bridged cyclic hydrocarbon group. A cyclocalkyl group can have 3-22, 3-12, or 3-8 ring carbons, referred to herein as $(C_3$-$C_{22})$cycloalkyl, $(C_3$-$C_{12})$cycloalkyl, or $(C_3$-$C_8)$cycloalkyl, respectively. A cycloalkyl group can also have one or more carbon-carbon double bond or carbon-carbon triple bond.

Exemplary monocyclic cycloalkyl groups include, but are not limited to, cyclopentanes (cyclopentyls), cyclopentenes (cyclopentenyls), cyclohexanes (cyclohexyls), cyclohexenes (cyclopexenyls), cycloheptanes (cycloheptyls), cycloheptenes (cycloheptenyls), cyclooctanes (cyclooctyls), cyclooctenes (cyclooctenyls), cyclononanes (cyclononyls), cyclononenes (cyclononenyls), cyclodecanes (cyclodecyls), cyclodecenes (cyclodecenyls), cycloundecanes (cycloundecyls), cycloundecenes (cycloundecenyls), cyclododecanes (cyclododecyls), and cyclododecenes (cyclododecenyls). Other exemplary cycloalkyl groups, including bicyclic, multicyclic, and bridged cyclic groups, include, but are not limited to, bicyclobutanes (bicyclobutyls), bicyclopentanes (bicyclopentyls), bicyclohexanes (bicyclohexyls), bicycleheptanes (bicycloheptyls, including bicyclo[2,2,1]heptanes (bicycle[2,2,1]heptyls) and bicycle[3,2,0]heptanes (bicycle[3,2,0]heptyls)), bicyclooctanes (bicyclooctyls, including octahydropentalene (octahydropentalenyl), bicycle[3,2,1]octane (bicycle[3,2,1]octyl), and bicylo[2,2,2]octane (bicycle[2,2,2]octyl)), and adamantanes (adamantyls). Cycloalkyl groups can be fused to other cycloalkyl saturated or unsaturated, aryl, or heterocyclyl groups.

The term "aryl" as used herein refers to a mono-, bi-, or other multi-carbocyclic aromatic ring system. The aryl can have 6-22, 6-18, 6-14, or 6-10 carbons, referred to herein as $(C_6$-$C_{22})$aryl, $(C_6$-$C_{18})$aryl, $(C_6$-$C_{14})$aryl, or $(C_6$-$C_{10})$aryl, respectively. The aryl group can optionally be fused to one or more rings selected from aryls, cycloalkyls, and heterocyclyls. The term "bicyclic aryl" as used herein refers to an aryl group fused to another aromatic or non-aromatic carbocylic or heterocyclic ring. Exemplary aryl groups include, but are not limited to, phenyl, tolyl, anthracenyl, fluorenyl, indenyl, azulenyl, and naphthyl, as well as benzo-fused carbocyclic moieties such as 5,6,7,8-tetrahydronaphthyl. Exemplary aryl groups also include, but are not limited to a monocyclic aromatic ring system, wherein the ring comprises 6 carbon atoms, referred to herein as "$(C_6)$aryl" or phenyl. The phenyl group can also be fused to a cyclohexane or cyclopentane ring to form another aryl.

The term "arylalkyl" as used herein refers to an alkyl group having at least one aryl substituent (e.g., -aryl-alkyl-). Exemplary arylalkyl groups include, but are not limited to, arylalkyls having a monocyclic aromatic ring system, wherein the ring comprises 6 carbon atoms, referred to herein as "$(C_6)$arylalkyl." The term "benzyl" as used herein refers to the group —CH$_2$-phenyl.

The term "heteroalkyl" refers to an alkyl group as described herein in which one or more carbon atoms is replaced by a heteroatom. Suitable heteroatoms include oxygen, sulfur, nitrogen, phosphorus, and the like. Examples of heteroalkyl groups include, but are not limited to, alkoxy, amino, thioester, and the like.

The terms "heteroalkenyl" and "heteroalkynyl" refer to unsaturated aliphatic groups analogous in length and possible substitution to the heteroalkyls described above, but that contain at least one double or triple bond, respectively.

The term "heterocycle" refers to cyclic groups containing at least one heteroatom as a ring atom, in some cases, 1 to 3 heteroatoms as ring atoms, with the remainder of the ring atoms being carbon atoms. Suitable heteroatoms include oxygen, sulfur, nitrogen, phosphorus, and the like. In some cases, the heterocycle may be 3- to 10-membered ring structures or 3- to 7-membered rings, whose ring structures include one to four heteroatoms. The term "heterocycle" may include heteroaryl groups, saturated heterocycles (e.g., cycloheteroalkyl) groups, or combinations thereof. The heterocycle may be a saturated molecule, or may comprise one or more double bonds. In some case, the heterocycle is a nitrogen heterocycle, wherein at least one ring comprises at least one nitrogen ring atom. The heterocycles may be fused to other rings to form a polycylic heterocycle. Thus, heterocycles also include bicyclic, tricyclic, and tetracyclic groups in which any of the above heterocyclic rings is fused to one or two rings independently selected from aryls, cycloalkyls, and heterocycles. The heterocycle may also be fused to a spirocyclic group.

Heterocycles include, for example, thiophene, benzothiophene, thianthrene, furan, tetrahydrofuran, pyran, isobenzofuran, chromene, xanthene, phenoxathiin, pyrrole, dihydropyrrole, pyrrolidine, imidazole, pyrazole, pyrazine, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, triazole, tetrazole, oxazole, isoxazole, thiazole, isothiazole, phenanthridine, acridine, pyrimidine, phenanthroline, phenazine, phenarsazine, phenothiazine, furazan, phenoxazine, pyrrolidine, oxolane, thiolane, oxazole, oxazine, piperidine, homopiperidine (hexamethyleneimine), piperazine (e.g., N-methyl piperazine), morpholine, lactones, lactams such as azetidinones and pyrrolidinones, sultams, sultones, other saturated and/or unsaturated derivatives thereof, and the like.

In some cases, the heterocycle may be bonded to a compound via a heteroatom ring atom (e.g., nitrogen). In some cases, the heterocycle may be bonded to a compound via a carbon ring atom. In some cases, the heterocycle is pyridine, imidazole, pyrazine, pyrimidine, pyridazine, acridine, acridin-9-amine, bipyridine, naphthyridine, quinoline, isoquinoline, benzoquinoline, benzoisoquinoline, phenanthridine-1,9-diamine, or the like.

The term "heteroaromatic" or "heteroaryl" as used herein refers to a mono-, bi-, or multi-cyclic aromatic ring system containing one or more heteroatoms, for example 1-3 heteroatoms, such as nitrogen, oxygen, and sulfur. Heteroaryls can also be fused to non-aromatic rings. In various embodiments, the term "heteroaromatic" or "heteroaryl," as used herein except where noted, represents a stable 5- to 7-membered monocyclic, stable 9- to 10-membered fused bicyclic, or stable 12- to 14-membered fused tricyclic heterocyclic ring system which contains an aromatic ring that contains at least one heteroatom selected from the group consisting of N, O, and S. In some embodiments, at least one nitrogen is in the aromatic ring.

Heteroaromatics or heteroaryls can include, but are not limited to, a monocyclic aromatic ring, wherein the ring comprises 2-5 carbon atoms and 1-3 heteroatoms, referred to herein as "$(C_2$-$C_5)$heteroaryl." Illustrative examples of monocyclic heteroaromatic (or heteroaryl) include, but are not limited to, pyridine (pyridinyl), pyridazine (pyridazinyl), pyrimidine (pyrimidyl), pyrazine (pyrazyl), triazine (triazinyl), pyrrole (pyrrolyl), pyrazole (pyrazolyl), imidazole (imidazolyl), (1,2,3)- and (1,2,4)-triazole ((1,2,3)- and (1,2,4)-triazolyl), pyrazine (pyrazinyl), pyrimidine (pyrimidinyl), tetrazole (tetrazolyl), furan (furyl), thiophene (thienyl), isoxazole (isoxazolyl), thiazole (thiazolyl), isoxazole (isoxazolyl), and oxazole (oxazolyl).

The term "bicyclic heteroaromatic" or "bicyclic heteroaryl" as used herein refers to a heteroaryl group fused to another aromatic or non-aromatic carbocylic or heterocyclic ring. Exemplary bicyclic heteroaromatics or heteroaryls include, but are not limited to 5,6- or 6,6-fused systems, wherein one or both rings contain heteroatoms. The term "bicyclic heteroaromatic" or "bicyclic heteroaryl" also encompasses reduced or partly reduced forms of fused aromatic system wherein one or both rings contain ring heteroatoms. The ring system may contain up to three heteroatoms, independently selected from oxygen, nitrogen, and sulfur.

Exemplary bicyclic heteroaromatics (or heteroaryls) include, but are not limited to, quinazoline (quinazolinyl), benzoxazole (benzoxazolyl), benzothiophene (benzothiophenyl), benzoxazole (benzoxazolyl), benzisoxazole (benzisoxazolyl), benzimidazole (benzimidazolyl), benzothiazole (benzothiazolyl), benzofurane (benzofuranyl), benzisothiazole (benzisothiazolyl), indole (indolyl), indazole (indazolyl), indolizine (indolizinyl), quinoline (quinolinyl), isoquinoline (isoquinolinyl), naphthyridine (naphthyridyl), phthalazine (phthalazinyl), phthalazine (phthalazinyl), pteridine (pteridinyl), purine (purinyl), benzotriazole (benzotriazolyl), and benzofurane (benzofuranyl). In some embodiments, the bicyclic heteroaromatic (or bicyclic heteroaryl) is selected from quinazoline (quinazolinyl), benzimidazole (benzimidazolyl), benzothiazole (benzothiazolyl), indole (indolyl), quinoline (quinolinyl), isoquinoline (isoquinolinyl), and phthalazine (phthalazinyl). In certain embodiments, the bicyclic heteroaromatic (or bicyclic heteroaryl) is quinoline (quinolinyl) or isoquinoline (isoquinolinyl).

The term "tricyclic heteroaromatic" or "tricyclic heteroaryl" as used herein refers to a bicyclic heteroaryl group fused to another aromatic or non-aromatic carbocyclic or heterocyclic ring. The term "tricyclic heteroaromatic" or "tricyclic heteroaryl" also encompasses reduced or partly reduced forms of fused aromatic system wherein one or both rings contain ring heteroatoms. Each of the rings in the tricyclic heteroaromatic (tricyclic heteroaryl) may contain up to three heteroatoms, independently selected from oxygen, nitrogen, and sulfur.

Exemplary tricyclic heteroaromatics (or heteroaryls) include, but are not limited to, acridine (acridinyl), 9H-pyrido[3,4-b]indole (9H-pyrido[3,4-b]indolyl), phenanthridine (phenanthridinyl), pyrido[1,2-a]benzimidazole (pyrido[1,2-a]benzimidazolyl), and pyrido[1,2-b]indazole (pyrido[1,2-b]indazolyl).

The term "alkoxy" as used herein refers to an alkyl group attached to an oxygen (—O-alkyl-). "Alkoxy" groups also include an alkenyl group attached to an oxygen ("alkenyloxy") or an alkynyl group attached to an oxygen ("alkynyloxy") groups. Exemplary alkoxy groups include, but are not limited to, groups with an alkyl, alkenyl or alkynyl group of 1-22, 1-8, or 1-6 carbon atoms, referred to herein as $(C_1$-$C_{22})$alkoxy, $(C_1$-$C_8)$alkoxy, or $(C_1$-$C_6)$alkoxy, respectively. Exemplary alkoxy groups include, but are not limited to methoxy and ethoxy.

The term "cycloalkoxy" as used herein refers to a cycloalkyl group attached to an oxygen.

The term "aryloxy" or "aroxy" as used herein refers to an aryl group attached to an oxygen atom. Exemplary aryloxy groups include, but are not limited to, aryloxys having a monocyclic aromatic ring system, wherein the ring comprises 6 carbon atoms, referred to herein as "$(C_6)$aryloxy." The term "arylalkoxy" as used herein refers to an arylalkyl group attached to an oxygen atom. An exemplary aryalkyl group is benzyloxy group.

The term "amine" or "amino" as used herein refers to both unsubstituted and substituted amines, e.g., $NR_aR_bR_{b'}$, where $R_a$, $R_b$, and $R_{b'}$ are independently selected from alkyl, alkenyl, alkynyl, aryl, arylalkyl, carbamate, cycloalkyl, haloalkyl, heteroaryl, heterocyclyl, and hydrogen, and at least one of the $R_a$, $R_b$, and $R_{b'}$ is not hydrogen. The amine or amino can be attached to the parent molecular group through the nitrogen. The amine or amino also may be cyclic, for example any two of $R_a$, $R_b$, and $R_{b'}$ may be joined together and/or with the N to form a 3- to 12-membered ring (e.g., morpholino or piperidinyl). The term amino also includes the corresponding quaternary ammonium salt of any amino group. Exemplary amines include alkylamine, wherein at least one of $R_a$ $R_b$, or $R_{b'}$ is an alkyl group, or cycloalkylamine, wherein at least one of $R_a$ $R_b$, or $R_{b'}$ is a cycloalkyl group.

The term "ammonia" as used herein refers to $NH_3$.

The term "aldehyde" or "formyl" as used herein refers to —CHO.

The term "acyl" term as used herein refers to a carbonyl radical attached to an alkyl, alkenyl, alkynyl, cycloalkyl, heterocycyl, aryl, or heteroaryl. Exemplary acyl groups include, but are not limited to, acetyl, formyl, propionyl, benzoyl, and the like.

The term "amide" as used herein refers to the form —$NR_cC(O)(R_d)$— or —$C(O)NR_cR_e$, wherein $R_c$, $R_d$, and $R_e$ are each independently selected from alkyl, alkenyl, alkynyl, aryl, arylalkyl, cycloalkyl, haloalkyl, heteroaryl, heterocyclyl, and hydrogen. The amide can be attached to another group through the carbon, the nitrogen, $R_c$, $R_d$, or $R_e$. The amide also may be cyclic, for example $R_c$ and $R_e$, may be joined to form a 3- to 12-membered ring, such as a 3- to 10-membered ring or a 5- or 6-membered ring. The term "amide" encompasses groups such as sulfonamide, urea, ureido, carbamate, carbamic acid, and cyclic versions thereof. The term "amide" also encompasses an amide group attached to a carboxy group, e.g., -amide-COOH or salts such as -amide-COONa.

The term "arylthio" as used herein refers to an aryl group attached to an sulfur atom. Exemplary arylthio groups include, but are not limited to, arylthios having a monocyclic aromatic ring system, wherein the ring comprises 6 carbon atoms, referred to herein as "$(C_6)$arylthio."

The term "arylsulfonyl" as used herein refers to an aryl group attached to a sulfonyl group, e.g., —$S(O)_2$-aryl-. Exemplary arylsulfonyl groups include, but are not limited to, arylsulfonyls having a monocyclic aromatic ring system, wherein the ring comprises 6 carbon atoms, referred to herein as "$(C_6)$arylsulfonyl."

The term "carbamate" as used herein refers to the form —$R_fOC(O)N(R_g)$—, —$R_fOC(O)N(R_g)R_h$—, or —$OC(O)NR_gR_h$, wherein $R_f$, $R_g$, and $R_h$ are each independently selected from alkyl, alkenyl, alkynyl, aryl, arylalkyl, cycloalkyl, haloalkyl, heteroaryl, heterocyclyl, and hydrogen. Exemplary carbamates include, but are not limited to, arylcarbamates or heteroaryl carbamates (e.g., wherein at least one of $R_f$ $R_g$ and $R_h$ are independently selected from aryl or heteroaryl, such as pyridinyl, pyridazinyl, pyrimidinyl, and pyrazinyl).

The term "carbonyl" as used herein refers to —C(O)—.

The term "carboxy" or "carboxylate" as used herein refers to $R_j$—COOH or its corresponding carboxylate salts (e.g., $R_j$—COONa), where $R_j$ can independently be selected from alkoxy, aryloxy, alkyl, alkenyl, alkynyl, amide, amino, aryl, arylalkyl, cycloalkyl, ether, haloalkyl, heteroaryl, and heterocyclyl. Exemplary carboxys include, but are not limited to, alkyl carboxy wherein $R_j$ is alkyl, such as —O—C(O)-alkyl. Exemplary carboxy also include aryl or heteroaryl carboxy, e.g. wherein $R_j$ is an aryl, such as phenyl and tolyl, or heteroaryl group such as pyridine, pyridazine, pyrmidine and pyrazine. The term carboxy also includes "carboxycarbonyl," e.g. a carboxy group attached to a carbonyl group, e.g., —C(O)—COOH or salts, such as —C(O)—COONa.

The term "dicarboxylic acid" as used herein refers to a group containing at least two carboxylic acid groups such as saturated and unsaturated hydrocarbon dicarboxylic acids and salts thereof. Exemplary dicarboxylic acids include alkyl dicarboxylic acids. Dicarboxylic acids include, but are not limited to succinic acid, glutaric acid, adipic acid, suberic acid, sebacic acid, azelaic acid, maleic acid, phthalic acid, aspartic acid, glutamic acid, malonic acid, fumaric acid, (+)/(−)-malic acid, (+)/(−) tartaric acid, isophthalic acid, and terephthalic acid. Dicarboxylic acids further include carboxylic acid derivatives thereof, such as anhydrides, imides, hydrazides (for example, succinic anhydride and succinimide).

The term "cyano" as used herein refers to —CN.

The term "ester" refers to the structure —C(O)O—, —C(O)O—$R_i$—, —$R_j$C(O)O—$R_i$—, or —$R_j$C(O)O—, where O is not bound to hydrogen, and $R_i$ and $R_j$ can independently be selected from alkoxy, aryloxy, alkyl, alkenyl, alkynyl, amide, amino, aryl, arylalkyl, cycloalkyl, ether, haloalkyl, heteroaryl, and heterocyclyl. $R_i$ can be a hydrogen, but $R_j$ cannot be hydrogen. The ester may be cyclic, for example the carbon atom and $R_j$, the oxygen atom and or $R_i$, or $R_i$ and $R_j$ may be joined to form a 3- to 12-membered ring. Exemplary esters include, but are not limited to, alkyl esters wherein at least one of $R_i$ or $R_j$ is alkyl, such as —O—C(O)-alkyl, —C(O)—O-alkyl-, and -alkyl-C(O)—O-alkyl-. Exemplary esters also include aryl or heteroaryl esters, e.g. wherein at least one of $R_i$ or $R_j$ is an aryl group, such as phenyl or tolyl, or a heteroaryl group, such as pyridine, pyridazine, pyrimidine or pyrazine, such as a nicotinate ester. Exemplary esters also include reverse esters having the structure —$R_j$C(O)O—, where the oxygen is bound to the parent molecule. Exemplary reverse esters include succinate, D-argininate, L-argininate, L-lysinate and D-lysinate. Esters also include carboxylic acid anhydrides and acid halides.

The term "ether" refers to the structure —$R_k$O—$R_l$—, where $R_k$ and $R_l$ can independently be alkyl, alkenyl, alkynyl, aryl, cycloalkyl, heterocyclyl, and ether. The ether can be attached to the parent molecular group through $R_k$ or $R_l$. Exemplary ethers include, but are not limited to, alkoxyalkyl and alkoxyaryl groups. Ethers also include polyethers, e.g., where one or both of $R_k$ and $R_l$ are ethers.

The terms "halo" or "halogen" or "hal" or "halide" as used herein refer to F, Cl, Br, or I.

The term "haloalkyl" as used herein refers to an alkyl group substituted with one or more halogen atoms. "Haloalkyls" also encompass alkenyl or alkynyl groups substituted with one or more halogen atoms.

The terms "hydroxy" and "hydroxyl" as used herein refers to —OH.

The term "hydroxyalkyl" as used herein refers to a hydroxy attached to an alkyl group.

The term "hydroxyaryl" as used herein refers to a hydroxy attached to an aryl group.

The term "ketone" as used herein refers to the structure —C(O)—$R_m$ (such as acetyl, —C(O)CH$_3$) or —$R_m$—C(O)—$R_n$—. The ketone can be attached to another group through $R_m$ or $R_n$. $R_m$ or $R_n$ can be alkyl, alkenyl, alkynyl, cycloalkyl, heterocyclyl or aryl, or $R_m$ or $R_n$ can be joined to form, for example, a 3- to 12-membered ring.

The term "monoester" as used herein refers to an analogue of a dicarboxylic acid wherein one of the carboxylic acids is functionalized as an ester and the other carboxylic acid is a free carboxylic acid or salt of a carboxylic acid. Examples of monoesters include, but are not limited to, to monoesters of succinic acid, glutaric acid, adipic acid, suberic acid, sebacic acid, azelaic acid, oxalic and maleic acid.

The term "nitro" as used herein refers to —NO$_2$.

The term "nitrate" as used herein refers to NO$_3^-$.

The term "perfluoroalkyl" as used herein refers to an alkyl group in which all of the hydrogen atoms have been replaced by fluorine atoms. Exemplary perfluoroalkyl groups include, but are not limited to, $C_1$-$C_5$ perfluoroalkyl, such as trifluoromethyl.

The term "perfluorocycloalkyl" as used herein refers to a cycloalkyl group in which all of the hydrogen atoms have been replaced by fluorine atoms.

The term "perfluoroalkoxy" as used herein refers to an alkoxy group in which all of the hydrogen atoms have been replaced by fluorine atoms.

The term "phosphate" as used herein refers to the structure —OP(O)O$_2^{2-}$, —$R_o$OP(O)O$_2^{2-}$, —OP(O)(OR$_q$)O$^-$, or —$R_o$OP(O)(OR$_p$)O$^-$, wherein $R_o$, $R_p$ and $R_q$ each independently can be alkyl, alkenyl, alkynyl, aryl, cycloalkyl, heterocyclyl, or hydrogen.

The term "sulfide" as used herein refers to the structure —$R_q$S—, where $R_q$ can be alkyl, alkenyl, alkynyl, aryl, arylalkyl, cycloalkyl, haloalkyl, heteroaryl, heterocyclyl. The sulfide may be cyclic, for example, forming a 3 to 12-membered ring. The term "alkylsulfide" as used herein refers to an alkyl group attached to a sulfur atom.

The term "sulfinyl" as used herein refers to the structure —S(O)O—, —$R_r$S(O)O—, —$R_r$S(O)OR$_s$—, or —S(O)OR$_s$—, wherein $R_r$ and $R_s$ can be alkyl, alkenyl, aryl, arylalkyl, cycloalkyl, haloalkyl, heteroaryl, heterocyclyl, hydroxyl. Exemplary sulfinyl groups include, but are not limited to, alkylsulfinyls wherein at least one of $R_r$ or $R_s$ is alkyl, alkenyl, or alkynyl.

The term "sulfonamide" as used herein refers to the structure —($R_t$)—N—S(O)$_2$—$R_v$— or —$R_t$($R_u$)N—S(O)$_2$—$R_v$, where $R_t$, $R_u$, and $R_v$ can be, for example, hydrogen, alkyl, alkenyl, alkynyl, aryl, cycloalkyl, and heterocyclyl. Exemplary sulfonamides include alkylsulfonamides (e.g., where $R_v$ is alkyl), arylsulfonamides (e.g., where $R_v$ is aryl), cycloalkyl sulfonamides (e.g., where $R_v$ is cycloalkyl), and heterocyclyl sulfonamides (e.g., where $R_v$ is heterocyclyl).

The term "sulfonate" as used herein refers to a salt or ester of a sulfonic acid. The term "sulfonic acid" refers to $R_w$SO$_3$H, where $R_w$ is alkyl, alkenyl, alkynyl, aryl, cycloalkyl, or heterocyclyl (e.g., alkylsulfonyl). The term "sulfonyl" as used herein refers to the structure $R_x$SO$_2$—, where $R_x$ can be alkyl, alkenyl, alkynyl, aryl, cycloalkyl, and heterocyclyl (e.g., alkylsulfonyl). The term "alkylsulfonyl" as used herein refers to an alkyl group attached to a sulfonyl group. "Alkylsulfonyl" groups can optionally contain alkenyl or alkynyl groups.

The term "sulfonate" as used herein refers $R_w$SO$_3^-$, where $R_w$ is alkyl, alkenyl, alkynyl, cycloalkyl, aryl, heterocyclyl, hydroxyl, alkoxy, aroxy, or aralkoxy, where each of the alkyl, alkenyl, alkynyl, cycloalkyl, aryl, heteroaryl, alkoxy, aroxy, or aralkoxy optionally is substituted. Non-limiting examples include triflate (also known as trifluoromethanesulfonate, CF$_3$SO$_3^-$), benzenesulfonate, tosylate (also known as toluenesulfonate), and the like.

The term "thioketone" refers to the structure —$R_y$—C(S)—$R_z$—. The ketone can be attached to another group through $R_y$ or $R_z$. $R_y$ or $R_z$ can be alkyl, alkenyl, alkynyl, cycloalkyl, heterocyclyl or aryl, or $R_y$ or $R_z$ can be joined to form a ring, for example, a 3- to 12-membered ring.

Each of the above groups may be optionally substituted. As used herein, the term "substituted" is contemplated to include all permissible substituents of organic compounds, "permissible" being in the context of the chemical rules of valence known to those of ordinary skill in the art. It will be understood that "substituted" also includes that the substitution results in a stable compound, e.g., which does not spontaneously undergo transformation such as by rearrangement, cyclization, elimination, etc. In some cases, "substituted" may generally refer to replacement of a hydrogen with a substituent as described herein. However, "substituted," as used herein, does not encompass replacement and/or alteration of a functional group by which a molecule is identified, e.g., such that the "substituted" functional group becomes, through substitution, a different functional group. For example, a "substituted phenyl group" must still comprise the phenyl moiety and cannot be modified by substitution, in this definition, to become, e.g., a pyridine ring.

In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For purposes of the present teachings, the heteroatoms such as nitrogen may have hydrogen substituents and/or any permissible substituents of organic compounds described herein which satisfy the valencies of the heteroatoms.

In various embodiments, the substituent is selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide, and thioketone, each of which optionally is substituted with one or more suitable substituents. In some embodiments, the substituent is selected from alkoxy, aryloxy, alkyl, alkenyl, alkynyl, amide, amino, aryl, arylalkyl, carbamate, carboxy, cycloalkyl, ester, ether, formyl, haloalkyl, heteroaryl, heterocyclyl, ketone, phosphate, sulfide, sulfinyl, sulfonyl, sulfonic acid, sulfonamide, and thioketone, wherein each of the alkoxy, aryloxy, alkyl, alkenyl, alkynyl, amide, amino, aryl, arylalkyl, carbamate, carboxy, cycloalkyl, ester, ether, formyl, haloalkyl, heteroaryl, heterocyclyl, ketone, phosphate, sulfide, sulfinyl, sulfonyl, sulfonic acid, sulfonamide, and thioketone can be further substituted with one or more suitable substituents.

Examples of substituents include, but are not limited to, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, thioketone, ester, heterocyclyl, —CN, aryl, aryloxy, perhaloalkoxy, aralkoxy, heteroaryl, heteroaryloxy, heteroarylalkyl, heteroaralkoxy, azido, alkylthio, oxo, acylalkyl, carboxy esters, carboxamido, acyloxy, aminoalkyl, alkylaminoaryl, alkylaryl, alkylaminoalkyl, alkoxyaryl, arylamino, aralkylamino, alkyl sulfonyl, carboxamidoalkylaryl, carboxamidoaryl, hydroxyalkyl, haloalkyl, alkylaminoalkylcarboxy, aminocarboxamidoalkyl, cyano, alkoxyalkyl, perhaloalkyl, arylalkyloxyalkyl, and the like. In some embodiments, the substituent is selected from cyano, halogen, hydroxyl, and nitro.

As a non-limiting example, in various embodiments when one of the $R_a$, $R_b$, and $R_{b'}$ in $NR_aR_bR_{b'}$, referred to herein as an amine or amino, is selected from alkyl, alkenyl, alkynyl, cycloalkyl, and heterocyclyl, each of the alkyl, alkenyl, alkynyl, cycloalkyl, and heterocyclyl independently can be optionally substituted with one or more substituents each independently selected from alkoxy, aryloxy, alkyl, alkenyl, alkynyl, amide, amino, aryl, arylalkyl, carbamate, carboxy, cycloalkyl, ester, ether, formyl, haloalkyl, heteroaryl, heterocyclyl, ketone, phosphate, sulfide, sulfinyl, sulfonyl, sulfonic acid, sulfonamide, and thioketone, wherein each of the alkoxy, aryloxy, alkyl, alkenyl, alkynyl, amide, amino, aryl, arylalkyl, carbamate, carboxy, cycloalkyl, ester, ether, formyl, haloalkyl, heteroaryl, heterocyclyl, ketone, phosphate, sulfide, sulfinyl, sulfonyl, sulfonic acid, sulfonamide, and thioketone can be further substituted with one or more suitable substituents. In some embodiments when the amine is an alkyl amine or a cycloalkylamine, the alkyl or the cycloalkyl can be substituted with one or more substituents each independently selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide, and thioketone. In certain embodiments when the amine is an alkyl amine or a cycloalkylamine, the alkyl or the cycloalkyl can be substituted with one or more substituents each independently selected from amino, carboxy, cyano, and hydroxyl. For example, the alkyl or the cycloalkyl in the alkyl amine or the cycloalkylamine is substituted with an amino group, forming a diamine.

As used herein, a "suitable substituent" refers to a group that does not nullify the synthetic or pharmaceutical utility of the compounds of the invention or the intermediates useful for preparing them. Examples of suitable substituents include, but are not limited to: $(C_1-C_{22})$, $(C_1-C_8)$, $(C_1-C_6)$, or $(C_1-C_4)$ alkyl, alkenyl or alkynyl; $(C_6-C_{22})$, $(C_6-C_{18})$, $(C_6-C_{14})$, or $(C_6-C_{10})$ aryl; $(C_2-C_{21})$, $(C_2-C_{17})$, $(C_2-C_{13})$, or $(C_2-C_9)$ heteroaryl; $(C_3-C_{22})$, $(C_3-C_{12})$, or $(C_3-C_8)$ cycloalkyl; $(C_1-C_{22})$, $(C_1-C_8)$, $(C_1-C_6)$, or $(C_1-C_4)$ alkoxy; $(C_6-C_{22})$, $(C_6-C_{18})$, $(C_6-C_{14})$, or $(C_6-C_{10})$ aryloxy; —CN; —OH; oxo; halo; carboxy; amino, such as —NH$((C_1-C_{22})$, $(C_1-C_8)$, $(C_1-C_6)$, or $(C_1-C_4)$ alkyl), —N$((C_1-C_{22})$, $(C_1-C_8)$, $(C_1-C_6)$, or $(C_1-C_4)$ alkyl)$_2$, —NH$((C_6)$aryl), or —N$((C_6-C_{10})$ aryl)$_2$; formyl; ketones, such as —CO$((C_1-C_{22})$, $(C_1-C_8)$, $(C_1-C_6)$, or $(C_1-C_4)$ alkyl), —CO$(((C_6-C_{10})$ aryl) esters, such as —CO$_2((C_1-C_{22})$, $(C_1-C_8)$, $(C_1-C_6)$, or $(C_1-C_4)$ alkyl) and —CO$_2((C_6-C_{10})$ aryl). One of skill in art can readily choose a suitable substituent based on the stability and pharmacological and synthetic activity of the compound of the invention.

Unless otherwise specified, the chemical groups include their corresponding monovalent, divalent, trivalent, and tetravalent groups. For example, methyl includes monovalent methyl (—CH$_3$), divalent methyl (—CH$_2$—, methylyl), trivalent methyl

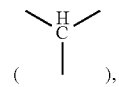

and tetravalent methyl

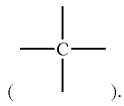

Unless otherwise specified, all numbers expressing quantities of ingredients, reaction conditions, and other properties or parameters used in the specification and claims are to be understood as being modified in all instances by the term "about." Accordingly, unless otherwise indicated, it should be understood that the numerical parameters set forth in the following specification and attached claims are approximations. At the very least, and not as an attempt to limit the application of the doctrine of equivalents to the scope of the claims, numerical parameters should be read in light of the number of reported significant digits and the application of ordinary rounding techniques. For example, the term "about" can encompass variations of ±10%, ±5%, ±2%, ±1%, ±0.5%, or ±0.1% of the numerical value of the number, which the term "about" modifies. In various embodiments, the term "about" encompasses variations of ±5%, ±2%, ±1%, or ±0.5% of the numerical value of the number. In some embodiments, the term "about" encompasses variations of ±5%, ±2%, or ±1% of the numerical value of the number. In certain embodiments, the term "about" encompasses variations of ±5% of the numerical value of the number. In certain embodiments, the term "about" encompasses variations of ±2% of the numerical value of the number. In certain embodiments, the term "about" encompasses variations of ±1% of the numerical value of the number.

All numerical ranges herein include all numerical values and ranges of all numerical values within the recited range of numerical values. As a non-limiting example, ($C_1$-$C_6$) alkyls also include any one of $C_1$, $C_2$, $C_3$, $C_4$, $C_5$, $C_6$, ($C_1$-$C_2$), ($C_1$-$C_3$), ($C_1$-$C_4$), ($C_1$-$C_5$), ($C_2$-$C_3$), ($C_2$-$C_4$), ($C_2$-$C_5$), ($C_2$-$C_6$), ($C_3$-$C_4$), ($C_3$-$C_5$), ($C_3$-$C_6$), ($C_4$-$C_5$), ($C_4$-$C_6$), and ($C_5$-$C_6$) alkyls.

Further, while the numerical ranges and parameters setting forth the broad scope of the disclosure are approximations as discussed above, the numerical values set forth in the Examples section are reported as precisely as possible. It should be understood, however, that such numerical values inherently contain certain errors resulting from the measurement equipment and/or measurement technique.

LIST OF ABBREVIATIONS AND TERMS

1H-NMR: Proton Nuclear Magnetic Resonance spectroscopy
ADME: Absorption, Distribution, Metabolism, and Excretion
AE: Adverse event
$AUC_{0-24}$: area under the concentration-time curve from time 0 to 24 hours postdose
BBB: blood-brain barrier
Cmax: maximum plasma concentration
cGMP: cyclic guanosine monophosphate
DMSO: dimethyl sulfoxide
DSFC: dorsal skin-fold chambers
F cells: blood cells with fetal haemoglobin
FIH: first in human
FTIR: Fourier transform infrared spectroscopy
GC: gas chromatography
HBB: hemoglobin subunit beta
HbF: fetal hemoglobin
HBG: gamma-globin gene
HbS: sickle hemoglobin
hERG: human ether-à-go-go related gene
HPLC: high-performance liquid chromatography
HU: hydroxyurea
IC: inhibitory concentration
IC50: a half minimal inhibitory concentration
ICAM-1: intercellular adhesion molecule-1
ICH: International Conference on Harmonisation
ICP-MS: inductively coupled plasma mass spectroscopy
IV: intravenous
MAD: multiple-ascending dose
MTD: maximum tolerated dose
NO: nitric oxide
NOAEL: no-observed-adverse-effect level
PD: pharmacodynamic
PDE9: phosphodiester-9
PEG polyethylene glycol
PIC: Powder in capsule
PK: pharmacokinetic(s)
PKG: protein kinase G
RBC: red blood cell
RH: relative humidity
SCD: sickle cell disease
SD: standard deviation
SEM: standard error of the mean
sGC: soluble guanylyl cyclase
t½: half-life
TK: Toxicokinetic
Tmax: time of maximum concentration
VOC: vaso-occlusive crisis
WBC: white blood cell
w/w %: weight/weight percent

EXAMPLES

It will be appreciated that the following examples are intended to illustrate but not to limit the present invention. Various other examples and modifications of the foregoing description and examples will be apparent to a person skilled in the art after reading the disclosure without departing from the spirit and scope of the invention, and it is intended that all such examples or modifications be included within the scope of the appended claims. All publications and patents referenced herein are hereby incorporated by reference in their entirety.

Example 1. Synthesis of Compound P3.1

List of Abbreviations aq aqueous
NBS N-bromosuccinimide
Boc tert-Butoxycarbonyl
° C. degrees Celsius
CDI N,N-carbonyl dimidazole
$δ_H$ chemical shift in parts per million downfield from tetramethylsilane
DCM dichloromethane
DEAD diethyl azodicarboxylate
Dppf bis(diphenylphosphino)ferrocene
DIPEA N,N-diisopropylethylamine
DMF N,N-dimethylformamide
eq equivalent
ESI electrospray ionization
Et ethyl
EtOAc ethyl acetate
g gram(s)
HPLC high-performance liquid chromatography
h hours
Hz hertz
J coupling constant (in NMR spectrometry)
LCMS liquid chromatography mass spectrometry
LiHMDS Lithium bis(trimethylsilyl)amide
μ micro
m multiplet (spectral); meter(s); milli
$M^+$ parent molecular ion
Me methyl MeCN acetonitrile
MeOH methanol
MHz megahertz
min minute(s)
mL milliliter
MS mass spectrometry
MTBE Methyl-tert-butyl ether
N normal (equivalents per liter)
NaOH sodium hydroxide
NBS N-Bromosuccinimide
nm nanometer(s)
NMR nuclear magnetic resonance
PE petroleum ether bp: 60~90° C.
RT room temperature
s singlet (spectral)
t triplet (spectral)
T temperature
TEA triethylamine
TFA trifluoroacetic acid
THF tetrahydrofuran
TLC thin layer chromatography
TMS tetramethylsilane
TMS-Cl trimethylsilyl chloride
Tol toluene The compounds of the present invention may be prepared with methods disclosed in WO 2013/053690, WO 2013/110768 and/or WO 2017/005786. Alternatively, Compound P3.1, an S,S enantiomer of P3, may be synthesized with the method provided herein.

Compound P3.1

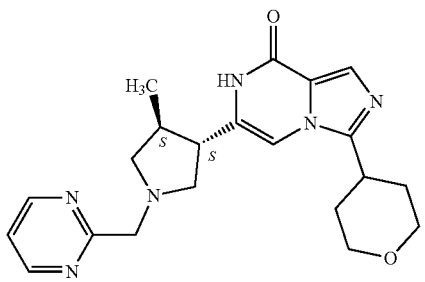

(Chemical Name: 6-[(3S,4S)-4-methyl-1-(pyrimidin-2-ylmethyl)pyrrolidin-3-yl]-3-tetrahydropyran-4-yl-7H-imidazo[1,5-a]pyrazin-8-one or (3S,4S)-6-(4-methyl-1-pyrimidin-2-ylmethyl-pyrrolidin-3-yl)-3-(tetrahydro-pyran-4-yl)-7H-imidazo[1,5-a]pyrazin-8-one)

The synthesis method provided in this application does not involve a chiral chromatographic separation of any intermediate or final product and the method also does not involve a separation of the racemic form of the final product. Chiral chromatographic separation, as used herein, means a process or technique for the separation of racemic compounds into their enantiomers. Examples of chiral chromatographic separation include chiral chromatography, such as chiral HPLC, simulated moving bed (SMB) chromatography, or chiral supercritical fluid chromatography (SFC). Chiral chromatography, such as chiral HPLC, when used to determine chiral purity, is not considered a chiral chromatographic separation in this regard.

In some embodiments, the synthesis method provided in this application involves resolution of a racemic mixture of an intermediate based on diastereomeric salt formation. Diastereomeric salts of the intermediate may be separated based on their different solubility. In some embodiments, washing and/or filtration techniques are used. Chiral chromatographic separation is not used to separate the diastereomeric salts.

In some embodiments, the synthesis method provided in this application uses a chiral acid. The chiral acid reacts with a racemic mixture of an intermediate to produce diastereomeric salts that can be separated, e.g., based on their solubility, without using any chiral chromatography separation. For example, the racemic mixture of Intermediate 2 (Rac-2) may react with a chiral acid to produce a solid intermediate comprising only the trans form of 2 (S,S-2). Non-limiting examples of chiral acids include, (+)-2,3-Dibenzoyl-D-tartaric acid≥99.0% (T), Dibenzoyl-L-tartaric acid 98%, (−)-O,O'-Di-p-toluoyl-L-tartaric acid 97%, (+)-O,O'-Di-p-toluoyl-D-tartaric acid, (+)-O,O'-Di-pivaloyl-D-tartaric acid, (−)-O,O'-Di-pivaloyl-D-tartaric acid, D-(−)-Tartaric acid, L-(+)-Tartaric acid, (4R)-2-Hydroxy-5,5-dimethyl-4-phenyl-1,3,2-dioxaphosphorinan 2-oxide 98%, L-(−)-Malic acid 97%, D-(+)-Malic acid, (R)-(−)-Mandelic acid, (S)-(+)-Mandelic acid, (R)-(−)-α-Methoxyphenylacetic acid, (S)-(+)-α-Methoxyphenylacetic acid, (R)-(+)-α-Methoxy-α-trifluoromethylphenylacetic acid, (S)-(−)-α-Methoxy-α-(trifluoromethyl)phenylacetic acid, (R)-(−)-2-Phenylpropionic acid, (S)-(+)-2-Phenylpropionic acid, (R)-1,4-Benzodioxane-2-carboxylic acid≥97.0% (sum of enantiomers, GC), (S)-1,4-Benzodioxane-2-carboxylic acid≥97.0% (sum of enantiomers, GC), (R)-(−)-1,1'-Binaphthyl-2,2'-diyl hydrogenphosphate≥98%, (S)-(+)-1,1'-Binaphthyl-2,2'-diyl hydrogenphosphate 97%, (1S)-(+)-3-Bromocamphor-10-sulfonic acid hydrate 98%, (1R)-(+)-Camphanic acid 98%, (1S)-(−)-Camphanic acid 98%, (1R,3S)-(+)-Camphoric acid 99%, (1S,3R)-(−)-Camphoric acid 99%, (1R)-(−)-10-Camphorsulfonic acid 98%, (1S)-(+)-10-Camphorsulfonic acid 99%, (R)-(−)-5-Oxo-2-tetrahydrofurancarboxylic acid, (S)-(+)-5-Oxo-2-tetrahydrofurancarboxylic acid, D-(−)-Quinic acid. A person of ordinary skill may perform any suitable method known in the art to screen and choose a chiral acid that results in a good chemical yield and high stereochemical purity. In one embodiment, the synthesis method provided in this application uses (+)-O,O-Dibenzoyl-D-tartaic acid.

The yield of Compound P3.1 is at least about 50%, about 60%, about 70%, about 80%, or about 90%. Yield, as used herein, means the ratio of the actual product weight and the theoretical product weight calculated from the amount of starting materials of a reaction. For example, the yield of Compound P3.1 synthesized from Intermediate 12 is the actual weight of Compound P3.1 divided by the theoretical weight of Compound P3.1 calculated from the amount of Intermediate 12.

The chiral purity of Compound P3.1 is above about 95.0%, about 96.0%, about 97.0%, about 98.0%, about 99.0%, about 99.5%, about 99.8%, or about 99.9%. Chiral purity of Compound P3.1 is calculated as the amount of pure (S,S) enantiomer divided by the total amount of all enantiomers. Chiral purity may be measured using any suitable technique, for example, chiral HPLC, a polarimeter, or chiral NMR-shift reagents.

The purity of Compound P3.1 is above about 95.0%, about 96.0%, about 97.0%, about 98.0%, about 99.0%, about 99.5%, about 99.8%, or about 99.9%. Purity of Compound P3.1 is calculated as the amount of Compound P3.1 divided by the total amount of the product including all impurities. The purity of Compound P3.1 may be determined by any suitable method such as HPLC, GC (gas chromatography), mass specification, or NMR.

Compound P3.1 prepared from the synthesis method disclosed in this application is substantially free of impurities. Impurities may include chemical impurities and/or physical impurities. Chemical impurities may include starting materials, intermediates, solvents, reagents and/or any byproduct. The level of impurities may be less than about 5%, about 2%, about 1%, about 0.5%, about 0.2%, or about 0.1%.

Synthesis of Compound P3.1 (also called (S,S)-P3) follows the following steps. The steps do not involve a chiral chromatography separation of the Intermediates Rac-2, (S,S)-2, (S,S)-3, (S,S)-4, (S,S)-10, (S,S)-11, (S,S)-12, or the final product P3.1.

Synthesis of Intermediate (S,S)-4

Synthesis of Intermediate 9

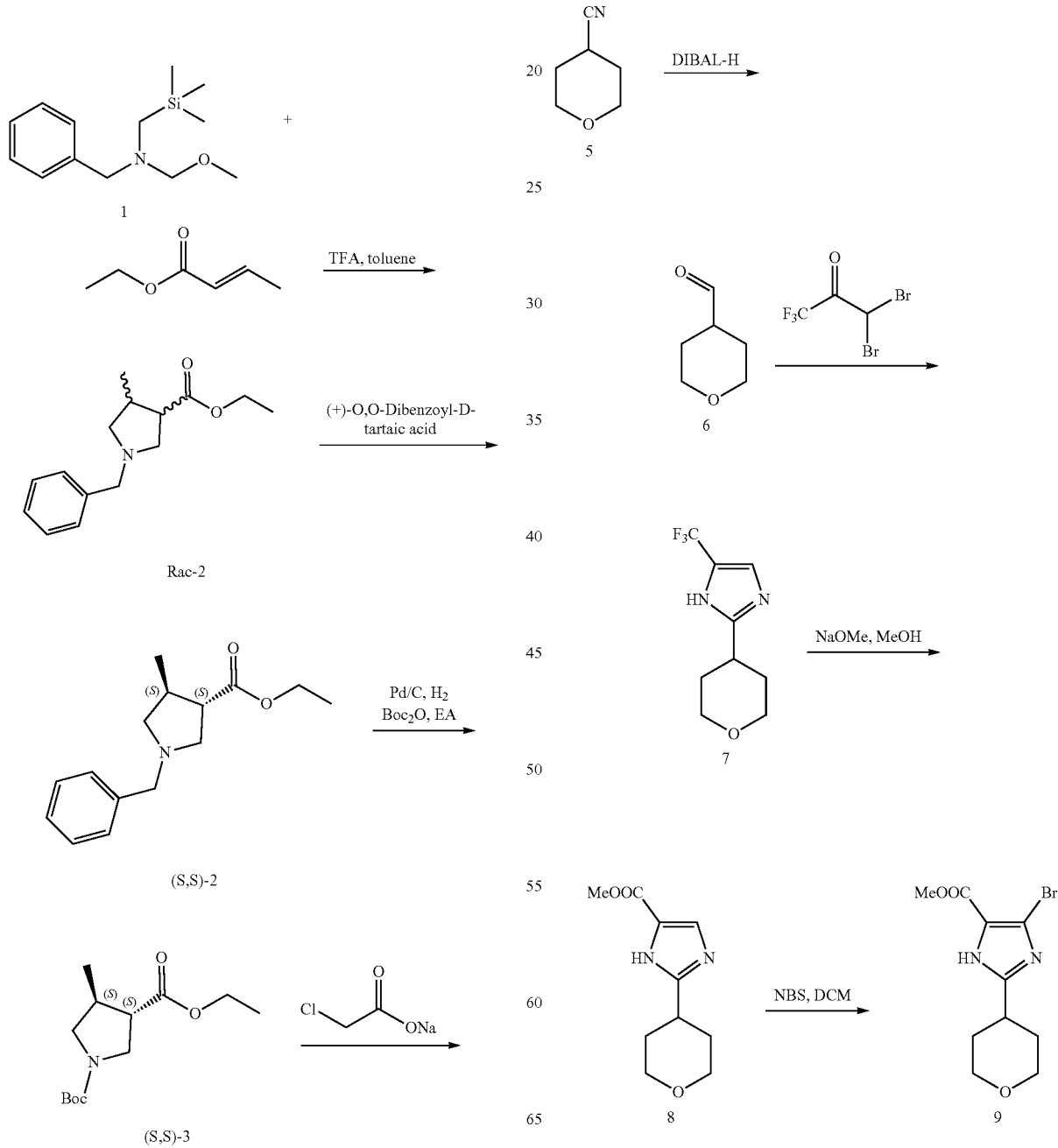

Synthesis of Final Compound P3.1
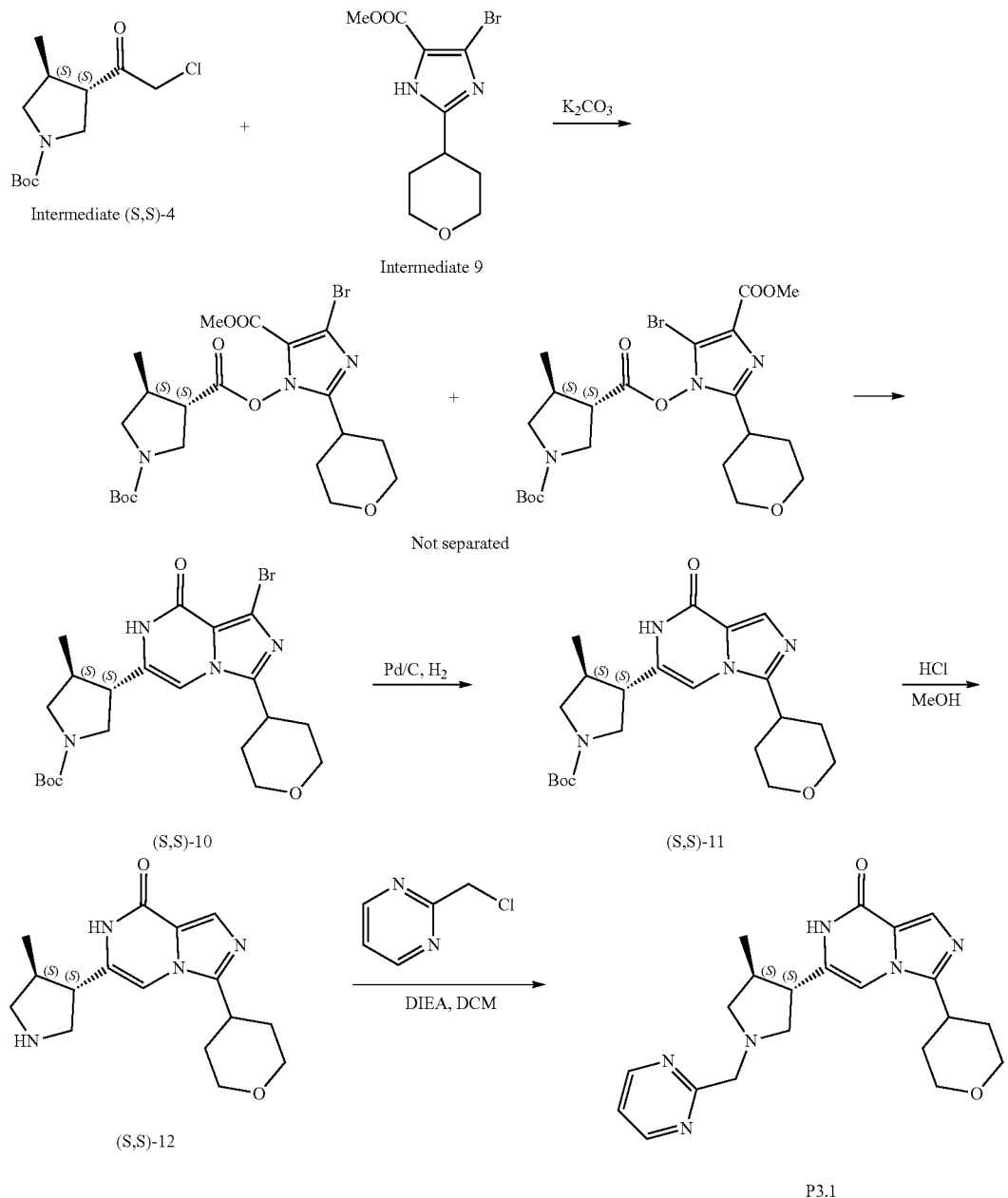
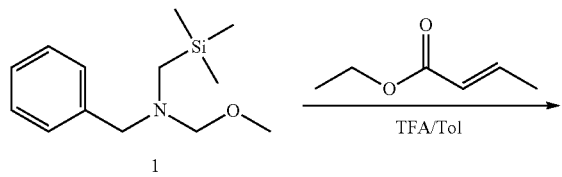
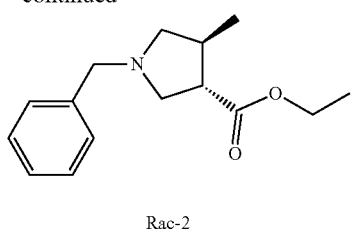
Rac-2
A solution of but-2-enoic acid ethyl ester (125 g, 1.10 mol) in toluene (1700 g) was prepared at 20° C. under nitrogen and TFA (7.68 g, 0.068 mol) was added while keeping the temperature below 25° C. Compound 1 (200 g, 0.84 mol) was added dropwise while keeping the reaction mixture below 35° C. (an exothermic reaction was observed) and the reaction was subsequently stirred for 2-5 hrs while keeping the temperature between 25-35° C. The nearly complete consumption of 1 was confirmed by HPLC (criterium: the ratio of 1:2 should be less than 3%) after which AcOH (5.60 g, 0.093 mol) was added while keeping the reaction temperature between 10-35° C. and the reaction was subsequently stirred for 30-60 mins at room temperature. 10% sodium carbonate solution (200 g) was added while keeping the reaction temperature between 10-35° C. and the resulting mixture was stirred for 1-3 hrs at room temperature. The phases were allowed to separate, the organic layer was isolated and evaporated to about 400-600 g while keeping the temperature below 70° C. yielding a solution of 2 in toluene which was analyzed by HPLC. Yields were generally in the range from 55-85%.

(3S,4S)-trans-1-benzyl-4-methyl-pyrrolidine-3-carboxylic acid ethyl ester (S,S)-(2)

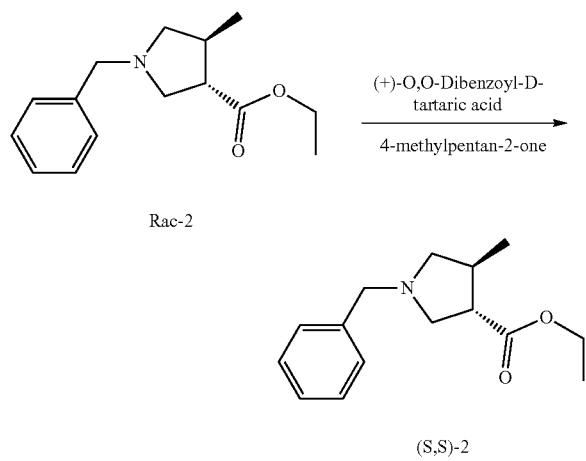

4-methylpentan-2-one (640 g) was loaded into a reactor at room temperature and stirred while the toluene solution of 2 (100 g, 0.404 mol) from the previous step was added under nitrogen. The reaction was evaporated to a total mass of 200-300 g while keeping the temperature below 65° C. and subsequently 4-methylpentan-2-one (160 g) was added followed by (−)-dibenzoyl-L-tartaric acid (94.1 g, 0.263 mol) and the resulting reaction mixture was heated to 65-75° C. and stirred at this temperature for 1-2 hrs. The reaction mixture was then cooled to 25-30° C. over a period of 5 hrs and then stirred at 25-30° C. for 3-5 hrs. The solid was filtered off and the filter cake was washed with 4-methylpentan-2-one (80 g). The filtrate was loaded into the reactor and 10% aqueous sodium carbonate (150 g) was added. The resulting reaction mixture was stirred for 1-2 hrs, the phases were separated and the aqueous phase was extracted with 4-methylpentan-2-one (40.5 g). The combined organic phases were washed with water (100 g); at this point a sample was analyzed by HPLC to confirm that the level of (−)-dibenzoyl-L-tartaric acid did not exceed 0.5%. The organic phase was then treated with (+)-dibenzoyl-D-tartaric acid (86.7 g, 0.242 mol) under nitrogen and the resulting reaction mixture was heated to 65-75° C. and kept at this temperature with stirring for 1-2 hrs. The reaction mixture was then cooled to 25-30° C. over 3 hrs and stirred at 25-30° C. for 3-5 hrs. The solid was filtered off and the cake was washed with 4-methylpentan-2-one (80 g). At this point the isolated solid was analyzed by chiral HPLC to confirm whether the chiral purity of (S,S)-2 was greater than 99.5% before proceeding.

If the chiral purity was less than 99.5% the following procedure was carried out: Ethanol (400 g) was loaded into the reactor, the isolated solid was added and the resulting reaction mixture was heated to 70-78° C. and stirred at this temperature for 1-4 hrs. The resulting solution was cooled to 20-25° C. over a period of 5-10 hrs and stirred at 20-25° C. for 1-5 hrs. The solid was filtered off and the cake was filtered off, washed with EtOH and dried. At this point the isolated solid was analyzed by chiral HPLC to confirm whether the chiral purity of (S,S)-2 was greater than 99.5% before proceeding. If the chiral purity was below 99.5% the recrystallization from EtOH was repeated.

10% Sodium carbonate solution (400 g) was loaded into the reactor and the solid cake was added followed by MTBE (488 g). The mixture was stirred for 30 minutes after which the phases were separated. The aqueous phase was charged into the reactor and MTBE (244 g) was added. The resulting mixture was stirred for 30 minutes after which the phases were separated. The combined organic phases were evaporated to a total mass of about 30-50 g at a temperature below 40° C. (S,S)-2 was isolated as an oil. HPLC analysis showed the yield to be in the range of 20-50% and the chiral purity to be greater than 99.5%.

Alternatively, (S,S)-2 can be prepared with asymmetric enzymatic hydrolysis. No chiral acid is used in this alternative method. The enzyme selectively hydrolyses the ester of only the unwanted (R,R)-2 enantiomer; the desired (S,S)-2 ester is left essentially unchanged. This step would replace the resolution using a chiral acid. The synthesis scheme is shown below. HLE stands for human leukocyte elastase, a serine protease enzyme. (R,R)-2, (S,S)-acid, and (R,R)-acid are byproducts.

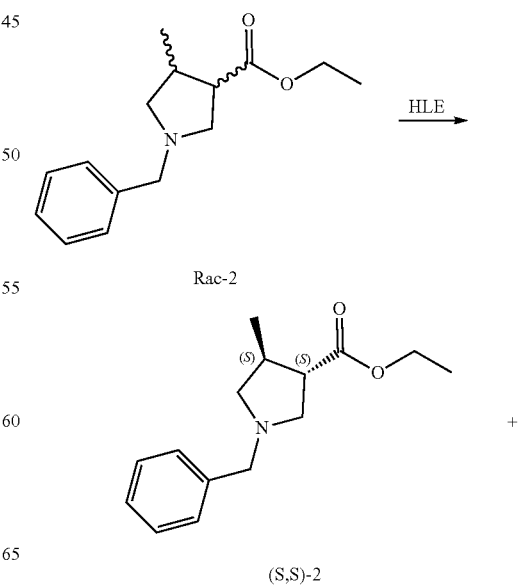

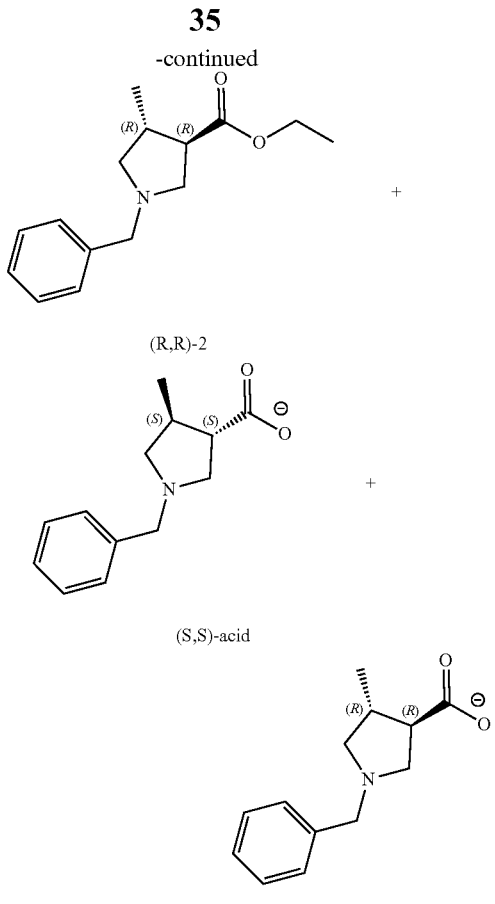

(R,R)-2

(S,S)-acid (R,R)-acid

Reaction condition: for each vial, 10 mg Rac-2 was dissolved in 0.1 mL MTBE, to which about 5 mg HLE enzyme and 1 mL buffer (pH=7) were added. Such mixture was incubated at 23 (20~25) ° C. for 24 h in an orbital shaker, then extracted by 1 mL dichloromethane (DCM). The upper layer (aqueous phase) was discarded, while the bottom layer (DCM phase) was evaporated by nitrogen flow and submitted for HPLC analysis. The extraction step removed the acid byproducts. The esters, (S,S)-2 and (R,R)-2, were extracted with DCM from the buffer solution, while the acid byproducts stayed in the aqueous phase.

Various enzymes were tested. The ratios between (S,S)-2 and (R,R)-2 were measured and enantiomeric excess (ee) were calculated. ee is a measurement of purity used for chiral substances. It reflects the degree to which a sample contains one enantiomer in greater amounts than the other.

| Condition | | Results | |
|---|---|---|---|
| Enzyme | Origin | ee | (R,R)-2 vs (S,S)-2 |
| H009018 | Lipase B from Candida antarctica | 96.2% | 1.9:98.1 |
| H609002 | Novozym 435 | 95.6% | 2.2:97.8 |
| H709099 | CaLB ImmoPlus | 94.4% | 2.8:97.2 |
| H519077 | Amano CES L-7 | 91.2% | 4.4:95.6 |
| H519055 | Amano CES P-2 | 85.0% | 7.5:92.5 |

The enzymes with the best ee were tested further to confirm stereospecificity. Reaction condition: for each vial, mix 500 mg Rac-2 with 10 mL buffer (pH=7) and 50 mg enzyme. Such mixture was incubated at 23 (20~25) ° C. for 24 h in an orbital shaker, then extracted by 2 mL DCM. The upper layer (aqueous phase) was discarded, while the bottom layer (DCM phase) was evaporated by nitrogen flow and submitted for HPLC analysis. The best enzymes gave stereospecificity (ee)>99%.

| Condition | | Results | |
|---|---|---|---|
| Enzyme | Origin | ee | (R,R)-2 vs (S,S)-2 |
| H609002 | Novozym 435 | 99.78% | 0.11:99.89 |
| H009018 | Lipase B from Candida antarctica | 99.82% | 0.09:99.91 |
| H519077 | Amano CES L-7 | 99.82% | 0.09:99.91 |
| H709099 | CaLB ImmoPlus | 99.96% | 0.02:99.98 |

Further tests were carried out to get higher yield, e.g., by shrinking the reaction volume by reducing the buffer loading. Reaction condition: for each vial, mix 0.1, 0.2, 0.5, 1, 2 g Rac-2 with 2 mL buffer (pH=7) and 0.1×enzyme. Such mixture was incubated at 23 (20~25) ° C. for 24 h in an orbital shaker, then dissolved to 20 mL using EtOH. The mixture was filtered, and the filtrate was submitted for HPLC analysis of ee and assay. Although stereospecificity (ee) was >99%, the yield (in situ) was not high enough.

| Condition | Results | |
|---|---|---|
| Buffer | ee | Yield |
| 20 V | 100% | 35.8% |
| 10 V | 100% | 34.9% |
| 5 V | 99.8% | 36.0% |
| 2 V | 99.8% | 38.1% |
| 1 V | 94.1% | 46.7% |

Co-solvent was then screened for better in situ yield. MTBE was replaced with other solvents. Reaction condition: for each vial, 0.1 g Rac-2 was dissolved in 0.1 mL co-solvent, mixing with 0.9 mL buffer (pH=7) and 10 mg HLE enzyme. Such mixture was incubated at 23 (20~25) ° C. for 24 h in an orbital shaker, then dissolved to 5 mL using EtOH. The mixture was filtered, and the filtrate was submitted for analysis.

| Co-solvent | Yield (in situ) |
|---|---|
| ACN | 12.1% |
| 1,4-dioxane | 14.8% |
| DMF | 19.9% |
| DMSO | 20.1% |
| n-heptane | 5.0% |
| 2-MeTHF | 15.5% |
| MTBE | 7.9% |
| t-amyl alcohol | 24.9% |
| t-butanol | 15.1% |
| THF | 22.3% |
| Toluene | 4.3% |

Although the stereospecificity was good, yield (in situ) using enzymatic hydrolysis was not high enough (<40%), and co-solvent did not help improve the yield. Therefore, resolution using a chiral acid to prepare (S,S)-2 is preferred.

(3S,4S)-trans-4-methyl-pyrrolidine-1,3-dicarboxylic acid 1-tert-butyl ester (S,S)-(3)

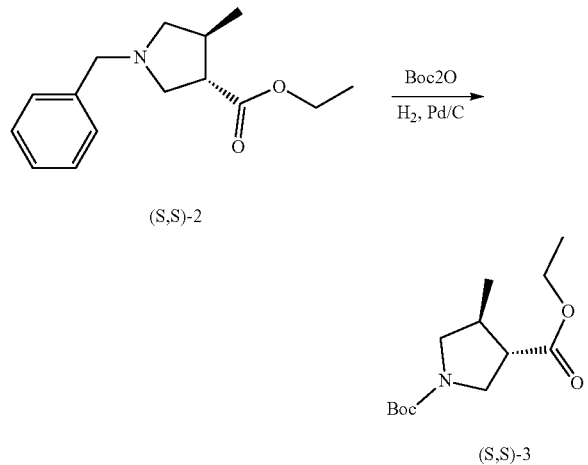

THF (700 g) was charged into the primary reactor R1 which had been previously purged with nitrogen. (S,S)-2 (100 g, 0.40 mol) was added at 20-25° C. and the reactor was evaporated and purged with nitrogen three times. Wet Pd/C (10%, 10 g) was added to the reactor at 20-25° C. and the reactor was evaporated and purged with hydrogen three times. The reaction mixture was subjected to hydrogenation with stirring at a pressure of 0.3-0.4 MPa and a temperature of 45-50° C. for 10-18° C. At this point an HPLC analysis was performed to verify that not more than 0.2% of the starting material remained. The reaction mixture was filtered through a plug of Celite (50-100 g) and the filter was washed with THF (230 g). The combined filtrates were transferred to the secondary reactor R2 and cooled to 0-10° C. Boc₂O (90 g, 0.41 mol) was charged into the reactor at 0-10° C. and the reaction mixture was warmed to 20-30° C. and stirred at this temperature for 1-4 hrs. At this point an HPLC analysis confirmed that not more than 1% of the debenzylated intermediate remained. The reaction mixture was concentrated in vacuo at less than 45° C. and THF (500 g) was added to the reactor. The resulting reaction mixture was evaporated in vacuo at a temperature below 45° C. to give the product (S,S)-3. HPLC analysis confirmed that the water content was less than 1%. The yield was generally in the range from 80-95%.

(3S,4S)-trans-3-(2-chloroacetyl)-4-methyl-pyrrolidine-1-carboxylic acid tert-butyl ester

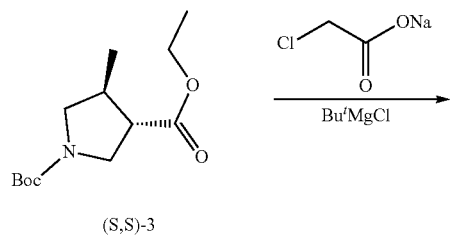

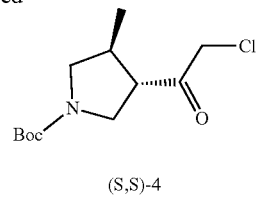

Sodium chloroacetate (68 g, 0.58 mol) was charged into a 5000 mL reactor R1 under nitrogen and dry THF (890 g) was added followed by (S,S)-3 (100 g, 0.39 mol). Triethylamine (58 g, 0.58 mol) was added after which the temperature was adjusted to −5° C. to 5° C. tert-Butylmagnesium chloride in THF (914 mL, 868.3 g, 4.0 eq.) was added dropwise over 1 hr while maintaining the reaction in the temperature interval −5° C. to 5° C. The reaction mixture was the warmed to 5-10° C. and stirred at this temperature for 2-5 hrs. At this point an HPLC analysis was performed to verify that the near complete consumption of the starting material. The temperature was readjusted to −5° to 5° C. and the reaction was quenched by the dropwise addition of a 15% (w/w) aqueous ammonium chloride solution (2200 g-2775 g) at −5° C. to 5° C. The temperature was adjusted to 0-5° C. and the resulting reaction mixture was stirred for 1-2 hrs after which it was allowed to stand for 2-3 hours to allow the phases to separate. The aqueous layer was transferred to a second reactor, R2, n-heptane (1000 mL) was added and the reactor was stirred at 0-5° C. for 0.5-1 hr after which it was allowed to stand for 0.5-1 hr. The aqueous layer was separated. The first reactor R1 containing the THF solution was charged with saturated aqueous sodium sulfate solution (10% (w/w), 100 g) at 0-5° C., the reactor was stirred for 0.5-1 hr at 0-5° C. after which it was allowed to stand for 0.5-1 hr at 0-5° C. The aqueous layer was transferred to the second reactor R2 and the organic phase in R1 was concentrated under vacuum to about 100-200 g at a temperature below 30° C. At the same time the second reactor R2 was stirred at 0-5° C. for 0.5-1 hr after which it was allowed to stand for 0.5-1 hr at 0-5° C. The aqueous phase was separated and the organic phase was transferred to R1. Saturated aq. Sodium sulphate (10% (w/w), 50-100 g) was added and the reactor was stirred at 0.5-1 hr at 0-5° C. after which it was allowed to stand for 0.5-1 hr at 0-5° C. The aqueous phase was separated and the organic phase was filtered through a plug of sodium sulphate (50-100 g). The organic filtrate was evaporated in vacuo at a temperature below 30° C. to give the product in a yield ranging from 60-100%.

Tetrahydropyran-4-carbaldehyde (6)

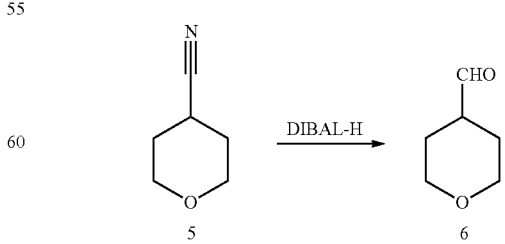

Dry toluene (500 g) was charged into a dried reactor under nitrogen and tetrahydropyran-4-carbonitrile 5 (100 g, 0.90 mol) was added. The resulting solution was cooled to −5° C. to 5° C. and a solution of DIBAL-H in toluene (1.0M, 800 g, 1.0 mol) was added dropwise at −5° C. to 5° C. and the resulting reaction mixture was stirred at this temperature for 1-2 hrs. The reaction mixture was then warmed to 20-25° C. and stirred at this temperature for 1-2 hrs. Subsequently the reaction mixture was cooled to −5° C.-5° C. and quenched by the dropwise addition of a solution of AcOH (195 g) in toluene (180 g) at −5°-5° C. (caution: exothermic, gas release). A 25% solution of sodium tartrate tetrahydrate (1000 g) was added slowly at −5° C.-5° C. (caution: exothermic, gas release). The reaction mixture was allowed to warm to 20-25° C. and stirred at this temperature for 8-16 hrs. The layers were separated and the aqueous layer was extracted twice with EtOAc (900 mL each) at 20-25° C. The two EtOAc extracts were combined with the original organic phase and the combined organic phases were evaporated in vacuo to about 100-200 g to yield the product 6. The product was generally isolated in 50-80% yield.

2-Tetrahydropyran-4-yl-5-(trifluoromethyl)-1H-imidazole (7)

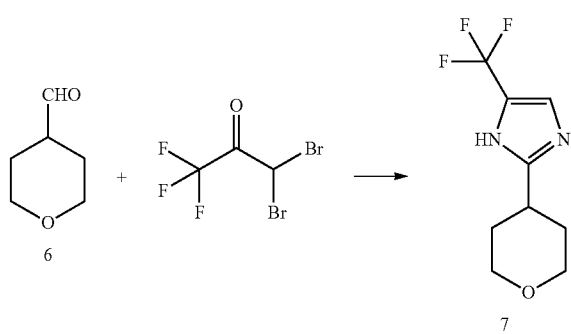 [SMILES: O=CC1CCOCC1 ; O=C(C(Br)Br)C(F)(F)F ; FC(F)(F)c1cnc(C2CCOCC2)[nH]1]

Water (730 g) was loaded into the main reactor R1 under nitrogen followed by sodium acetate (159 g, 1.94 mol) and 1,1-dibromo-3,3,3-trifluoroacetone (260 g, 0.96 mol) was added dropwise while keeping the reaction temperature between 20-30° C. The reaction mixture was then warmed to 80-85° C. and stirred at this temperature for 1-2 hrs after which it was cooled to 20-25° C. Compound 6 (100 g, 0.88 mol) was loaded into the secondary reactor R2 followed by MeOH (1150 g) and a 25% aqueous solution of ammonia (614 g, 4.38 mol) was added slowly while keeping the temperature in the range 15-30° C. The mixture in R1 was then added dropwise to R2 over 2 hrs at 15-30° C. The reaction was then stirred at 25-30° C. for 18-24 hrs. The reaction was then evaporated in vacuo at a temperature below 45° C. to around 500-800 g after which it was cooled to 25-30° C. and MTBE (100 g) was charged with stirring followed by heptanes (180 g); the reaction mixture was stirred at 20-30° C. for 2-3 hrs after which it was filtered. The filter was washed with water (320 g) and heptanes (120 g). At this point an HPLC analysis was performed to verify that the purity of 7 was greater than 96%. The filter cake was dried in vacuo at 40-45° C. for 8-24 hrs. At this point a Karl-Fischer titration showed that the water content was less than 0.5%. Compound 7 was generally isolated in 50-80%. Purity was greater than 96%.

Methyl 2-tetrahydropyran-4-yl-1H-imidazole-5-carboxylate (8)

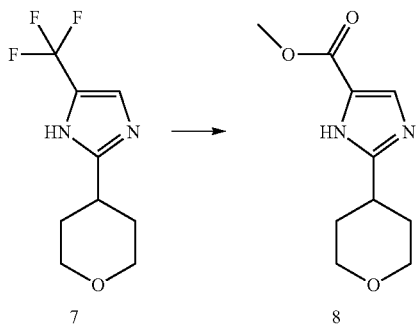

30% Sodium methoxide in methanol (245 g, 1.36 mol) was charged into the main reactor R1 under nitrogen and compound 7 (100 g, 0.45 mol) was added followed by MeOH (590 g) and the resulting reaction mixture was warmed to 60-65° C. and stirred for 5-10 hrs after which it was cooled to 20-30° C.; at this point an HPLC analysis confirmed that the level of 7 was below 1%. The reaction mixture was filtered and the filter was washed with MeOH (170 g). The filtrates were charged into the secondary reactor R2 under nitrogen and the pH was adjusted to 5-6 by dropwise addition of AcOH (30 g) at a temperature of 0-10° C. Water 150 g) was added while keeping the temperature in the range from 0-10° C. after which the reaction was warmed to 30-35° C. and stirred at this temperature for 6-18 hrs. The reaction mixture was concentrated in vacuo at a temperature below 40° C. around 200-300 g. Water (200 g) was added and the reaction was stirred for 1-2 hrs at 15-25° C. Solid sodium hydrogen carbonate (45 g) was added with stirring until the pH reached 7-8 and the reaction was stirred at 15-25° C. for 1-2 hrs. The resulting solid was filtered off, washed with water (100 g) and dried in vacuo at 40-45° C. for 18-24 hrs. Karl-Fischer titration confirmed that the water content was less than 1%. The product 8 was generally isolated in 70-90%.

Methyl 4-bromo-2-tetrahydropyran-4-yl-1H-imidazole-5-carboxylate (9)

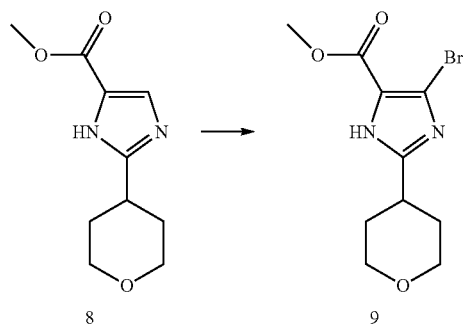 [SMILES: COC(=O)c1cnc(C2CCOCC2)[nH]1 ; COC(=O)c1[nH]c(C2CCOCC2)nc1Br]

Dichloromethane (1330 g) was charged into the primary reactor R1 and compound 8 (100 g, 0.475 mol) was charged into the reactor followed by N-Bromosuccinimide (84.7 g, 0.475 mol) while keeping the temperature in the range 20-25° C.; the reaction mixture was subsequently stirred at 20-25° C. for 1-5 hrs; at this point an HPLC analysis showed that less than 1% compound 8 remained. An aqueous solution of sodium carbonate (10%) and sodium sulfite (0.3%) (1100 g) was added at a temperature of 20-25° C. and the reaction was stirred at this temperature for 1-3 hrs. The organic (bottom) phase was transferred to the secondary reactor R2 and R1 was charged with dichloromethane (266 g) and stirred at 20-25° C. for 0.5-2 hrs. The bottom (organic) layer was charged into R2 followed by a 10% sodium carbonate solution (220 g) at 20-25° C. and the resulting mixture was stirred for 20-25° C. for 1-3 hrs. The bottom (organic) layer was transferred into R1 and dichloromethane (266 g) was charged into R2 which was stirred at 20-25° C. for 1-3 hrs). The bottom (organic) layer was transferred to R1 followed by 10% aqueous sodium carbonate solution (220 g). The resulting mixture was stirred for 20-25° C. for 1-3 hours after which the bottom (organic) layer was transferred to the now empty R2. R1 was charged with dichloromethane (266 g), the reaction mixture was stirred at 20-25° C. for 1-3 hrs and the bottom (organic) layer was transferred to R2. R2 was concentrated in vacuo to 100-200 g at a temperature below 40° C. The residue was cooled to 20-25° C. and heptanes (200 g) was added. The resulting mixture was stirred at 20-25° C. for 3-12 hrs, and the solid was filtered off and dried in vacuo at 40-45° C. for 20-24 hrs. A Karl-Fischer titration confirmed that the water content was less than 0.5%. The yield of 9 was generally in the range 70-100%.

(3S,4S)-3-(1-bromo-8-oxo-3-tetrahydropyran-4-yl)-7H-imidazo[1,5-a]pyrazin-6-yl)-4-methyl-pyrrolidine-1-carboxylic acid tert-butyl ester (S,S)-(10)

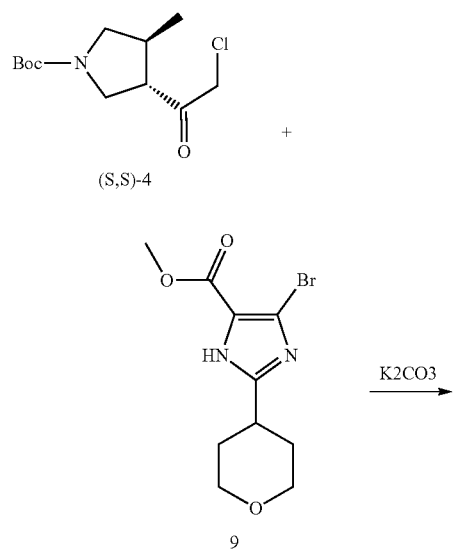

-continued

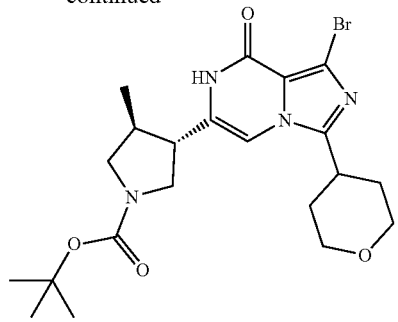

(S,S)-10

NMP (516 g) was charged into the primary reactor R1 under nitrogen followed by compound 9 (100 g, 0.346 mol). Potassium carbonate (72 g, 0.519 mol) and potassium iodide (5.74 g, 0.035 mol) was added and the resulting reaction mixture was cooled to −5°-5° C. with stirring. Compound (S,S)-4 (109 g, 0.415 mol) was dissolved in MTBE (152 g) and added dropwise at −5° C.-5° C. and stirred at this temperature for 12-16 hrs. An HPLC analysis at this point confirmed that compound 9 levels were below 1%. Diatomite (50-100 g) was charged into the reactor and the resulting mixture was stirred at −5° C.-5° C. for 1-2 hrs and filtered. The filter was washed with MTBE (152 g). The combined filtrates were transferred to the secondary reactor R2 and evaporated in vacuo below 40° C. to 500-600 g and the residue was cooled to 20-30° C. Ammonium acetate (107 g, 0.345 mol) was added at 10-30° C. under nitrogen and the resulting reaction mixture was warmed to 100-110° C. and stirred at this temperature for 12-16 hrs. At this point the reaction mixture was cooled to 20-30° C. and an HPLC analysis confirmed that the conversion of the uncyclized to cyclized product had taken place (i.e. less than 1% on the uncyclized intermediate remained). DCM (800 g) was charged into the reaction mixture at 20-30° C. followed by water (1000 g) at 20-30° C. The resulting mixture was stirred for 0.5-1 hrs and left to stand for 0.5-1 hr. The bottom layer was transferred to the primary reactor R1. DCM (400 g) was charged into R2 at 20-30° C., the resulting mixture was stirred for 0.5-1 hr and left to stand for 0.5-1 hr. The bottom layer was transferred to R1. The combined organic phases in R1 were treated with 10% aq. Sodium sulphate solution (300 g) at 20-30° C. and the resulting mixture was stirred for 0.5-1 hr and left to stand for 0.5-1 hr. The top layer (aqueous) was discarded. A 10% aq. Sodium sulphate solution (300 g) was charged into R1 at 20-30° C. and the resulting mixture was stirred for 0.5-1 hr and left to stand for 0.5-1 hr. The bottom (organic) layer was transferred to the now empty secondary reactor R2 and concentrated to about 200-300 g in vacuo at a temperature below 40° C. Water 1500-2000 g) was charged into R1 and the reaction mixture in R2 was added dropwise with stirring at 20-30° C. over 1 hr and the resulting mixture was stirred for 1-2 hrs. The solid was filtered off and washed with water (100 g). Isopropyl acetate (440 g) was charged into the primary reactor R1 at 20-30° C. and the wet cake was charged into R1 as well. The resulting mixture was warmed to 50-60° C. and stirred at this temperature for 2-4 hrs. The resulting reaction mixture was cooled to 20-30° C., the mixture was filtered and the filter was washed with isopropyl acetate (100 g). The solid was dried at 40-45° C. for 18-24 hrs. The yield of compound (S,S)-10 was generally in the range from 45-75%. The purity was better than 96%.

(3S,4S)-trans-6-(4-methyl-pyrrolidin-3-yl)-3-(tetra-hydro-pyran-4-yl)-7H-imidazo[1,5-a]pyrazin-8-one hydrochloride (3S,4S)-(12)

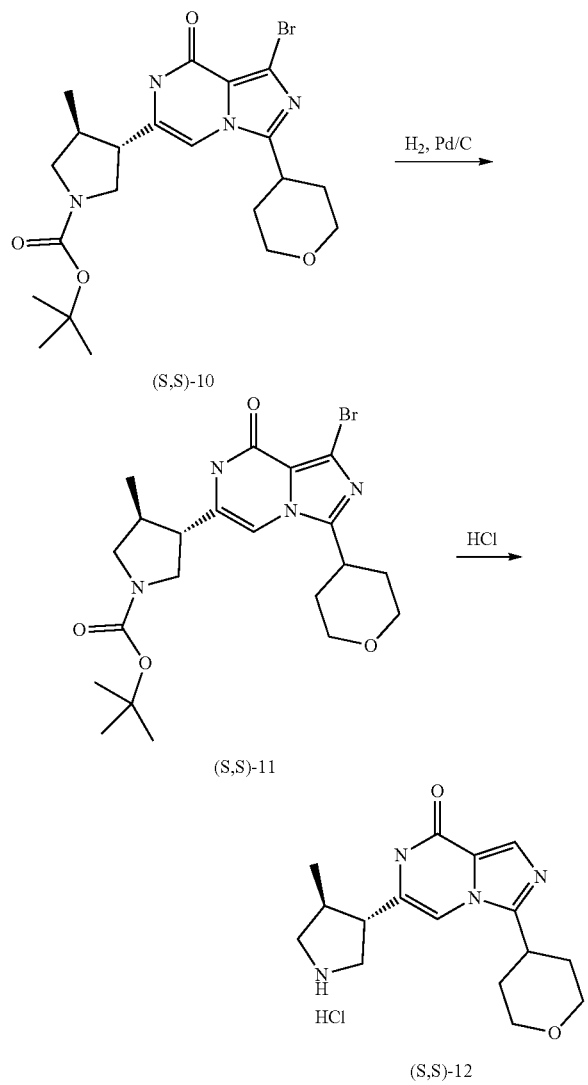

(3S,4S)-10 (100 g, 0.21 mol) was charged into the primary reactor R1 under nitrogen and MeOH (2400 g) was added. Pd/C catalyst (10%, 10 g) was loaded into the reactor under nitrogen and the resulting reaction mixture was subjected to hydrogenation (0.3-0.4 MPa) for for 12-24 hrs at 20-30° C. At this point an HPLC analysis was performed to verify that less than 1% of the starting material remained. The reaction mixture was filtered through a pad of Celite (50-100 g) and the Celite was washed with MeOH (200 g). The combined filtrates were charged into the secondary reactor R2 and evaporated in vacuo below 40° C. to about 400 mL. A solution of HCl (30-35 g) in MeOH (200 g) was charged dropwise into the reaction mixture at a temperature of 0-10° C. The reaction mixture was then warmed to 20-25° C. and stirred for 8-12 hrs at this temperature. An HPLC analysis at this stage served to verify that less than 1% of the intermediate (3S,4S)-11 remained in the solution. The reaction mixture was concentrated in vacuo at a temperature below 40° C. to a volume of around 200-250 mL. The reaction mixture was cooled to 20-25° C. and the resulting reaction mixture was added dropwise with stirring at 20-25° C. to EtOAc (1800 g) and the resulting mixture was stirred at 20-25° C. for 12-18 hrs. The solid was filtered off under a nitrogen atmosphere and washed with EtOAc (100 g). The solid was dried under a nitrogen flow at 20-30° C. for 18-24 hrs. The yield of (3S,4S)-12 was generally in the range from 70-100%.

(3S,4S)-trans-6-(4-methyl-1-pyrimidin-2-ylmethyl-pyrrolidin-3-yl)-3-(tetrahydro-pyran-4-yl)-7H-imidazo[1,5-a]pyrazin-8-one (P3.1)

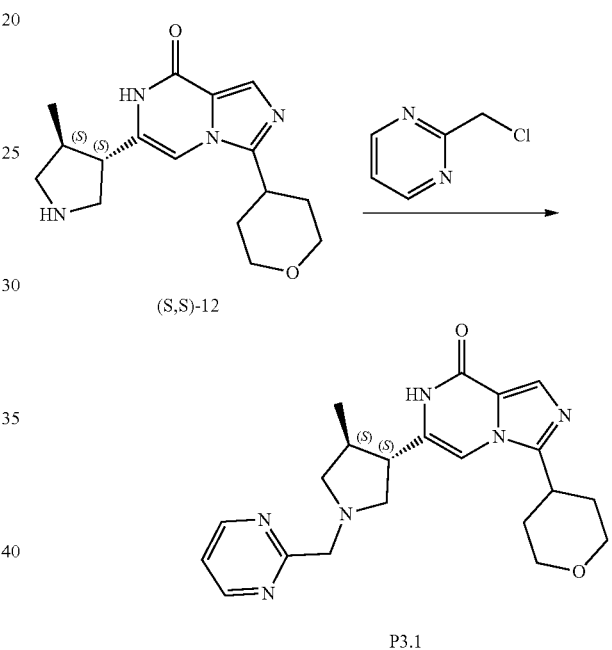

Dichloromethane (1330 g) was charged into the primary reactor R1 at room temperature under nitrogen and compound (S,S)-12 (100 g, 0.238 mol) was added followed by 2-chloromethylpyrimidine hydrochloride (47.2 g, 0.286 mol) and the reaction mixture was cooled to 0-10° C. with stirring. N,N-diisopropylethylamine (153 g, 1.19 mol) was added dropwise at a temperature of 0-10° C. and the reaction mixture was warmed to 20-30° C. and stirred at this temperature for 44-48 hrs. At this point an HPLC analysis was performed to confirmed that no more than 5% (S,S)-12 remained (in case this test failed a 3.9 g portion of 2-chloromethylpyrimidine hydrochloride was added and the reaction was stirred for another 44-48 hrs at 20-30° C.). Water (500 g) was added to the reaction mixture at 20-30° C. and the reaction was stirred at this temperature for 1-2 hrs. The bottom layer was transferred to the secondary reactor R2. Dichloromethane (266 g) was charged into R1 and the mixture was stirred for 1-2 hrs at 20-30° C. The bottom layer was transferred to R2 followed by water (200 g) and the reaction mixture was cooled to 0-10° C. The reactor was stirred while concentrated HCl (about 80 g) was added dropwise with stirring at a temperature of 0-10° C. until the pH of the reaction mixture reached 2-4 after which the reaction mixture was stirred at 0-10° C. for 1-2 hrs. The stirring was stopped and the phases were allowed to separate. The bottom layer was charged into the now empty R1 followed by water (100 g). R1 was stirred for 1-2 hrs at 0-10° C. after which the upper layer was transferred to R2. The reaction mixture in R2 was warmed to 10-20° C. and sodium carbonate (50 g) was charged slowly (caution: gas evolution) at 10-20° C. until a pH of 8-9 was reached. DCM (266 g) was charged into R2 and the reactor was stirred at 10-30° C. for 1-2 hrs. The bottom (organic) layer was transferred into R1. DCM (266 g) was charged into R2 and the reactor was stirred at 10-30° C. for 1-2 hrs. The bottom (organic) layer was transferred into R1. DCM (266 g) was charged into R2 and the reactor was stirred at 10-30° C. for 1-2 hrs. The bottom (organic) layer was transferred into R1. The mixture in R1 was filtered through a plug of sodium sulfate (50 g) into R2 and the filter was washed with DCM (133 g). The combined organic filtrates were concentrated in vacuo to around 266-400 g at a temperature below 45° C. Isopropanol (600 g) was charged into R2 and the resulting mixture was concentrated in vacuo at a temperature below 45° C. The resulting mixture was cooled to 20-30° C. and seed crystals (100 mg) were added. The resulting reaction mixture was stirred for 1-4 hrs at 20-30° C. Heptanes (100 g) was charged into the reaction mixture at 20-30° C. followed by seed crystals (100 mg). The resulting reaction mixture was stirred for 1-4 hrs at 20-30° C. Heptanes (300 g) was charged into the reaction mixture at 20-30° C. and the resulting reaction mixture was stirred for 6-12 hrs at 20-30° C. The solid was filtered off and washed with a mixture of isopropanol:heptanes (1:3, 100 g). The solid was dried in vacuo at 40-45° C. for 18-24 hrs. An HPLC analysis of the resulting solid confirmed a purity better than 97.5%. The yield of (S,S)-P3.1 was generally in the range 50-80%.

Example 2. Formulation of Compound P3.1

A stability study has been completed on Compound P3.1. Samples of Compound P3.1 were aliquoted into double-walled polyethylene pouches, which were tied off and then heat-sealed in an aluminum pouch. Samples were stored at ambient temperature and at 40° C.-45° C. (no humidity control) with testing performed over a 3-month period. There were no changes to appearance or purity of the material at either room temperature or accelerated conditions over the duration of the study, indicating that the drug substance is not readily affected by accelerated temperature conditions.

In another stability study, Compound P3.1 was dissolved at approximately 40 mg/mL of purified water and evaluated for purity over a period of 8 days. Samples were stored at both refrigerated and ambient conditions, and tested at T=0, Day 2, and Day 8. No significant change to the purity of the compound or appearance of the solution was observed over the course of the study.

In yet another stability study, the study design includes sample storage at both 25° C.±2° C./60% relative humidity (RH)±5% RH, as well as 40° C.±2° C./75% RH±5% RH. Samples are stored in bags comparable to those used for packaging of Compound P3.1. The study is designed to evaluate stability of Compound P3.1 for up to 6 months at the accelerated temperature and for 36 months at the defined storage temperature of 25° C.

Compound P3.1 packaging is prepared by direct filling of the compound into opaque white gelatin capsules (Powder in Capsule, PIC). No binders, bulking agents, or other excipients are added. The capsules contain between 10 and 100 mg of Compound P3.1.

The packaging is monitored in a 6 month to 36 month stability study. The conditions include 25° C./60% RH and 40° C./75% RH (6 months only). Testing includes Appearance, Assay and Related Substances, and Dissolution and Moisture Analysis. A 5° C. arm is also be included, but not tested unless there are indications of product instability at the 25° C. arm of the study.

Alternatively, the dosage form is prepared by blending Compound P3.1 with selected excipients. The excipients that may be used are summarized below in Table 2:

TABLE 2

| Proposed Excipients for Future Drug Product Manufacturing | |
|---|---|
| Excipient | Purpose |
| Pre-gelatinized Starch, NF | Filler, placebo |
| Microcrystalline Cellulose, NF | Filler, placebo |
| Colloidal Silicon Dioxide, NF | Glidant |
| Magnesium Stearate, NF (non-bovine) | Lubricant |

The invention claimed is:

1. A process for the synthesis of 6-((3S,4S)-4-methyl-1-(pyrimidin-2-ylmethyl)pyrrolidin-3-yl)-3-tetrahydropyran-4-yl-7H-imidazo[1,5-a]pyrazin-8-one of formula P3.1:

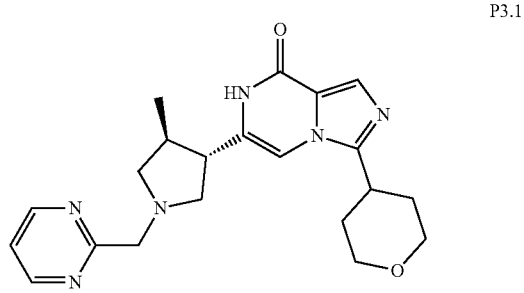 [SMILES: C[C@@H]1CN(Cc2ncccn2)C[C@H]1c1cn2c(C3CCOCC3)ncc2c(=O)[nH]1]

wherein the process comprises the following steps of:

(a) reacting a compound of formula (S,S)-4:

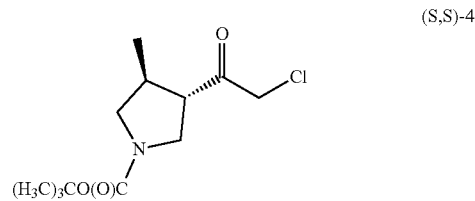

with a compound of formula 9:

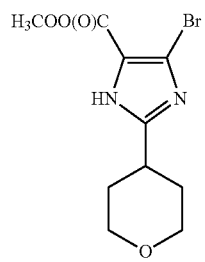

in the presence of potassium carbonate (K₂CO₃) followed by a reaction with ammonium acetate (NH₄OAc), to provide a compound of formula (S,S)-10:

(b) reacting the compound of formula (S,S)-10 above with hydrogen gas in the presence of a Pd/C catalyst, to provide a compound of formula (S,S)-11:

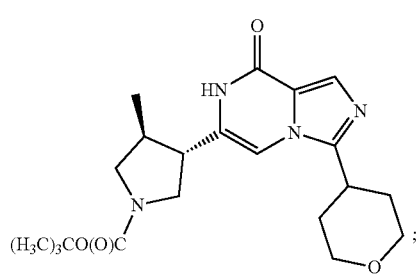

(c) reacting the compound of formula (S,S)-11 above with hydrochloric acid (HCl), to provide a compound of formula (S,S)-12:

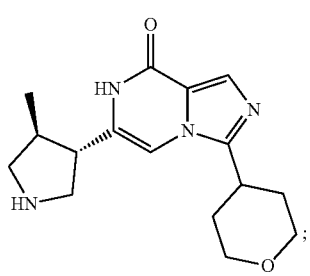

and (d) reacting the compound of formula (S,S)-12 above with a compound of the following formula:

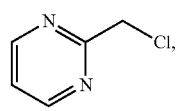

in the presence of N,N-diisopropylethylamine (DIPEA), to provide 6-((3S,4S)-4-methyl-1-(pyrimidin-2-ylmethyl)pyrrolidin-3-yl)-3-tetrahydropyran-4-yl-7H-imidazo[1,5-a]pyrazin-8-one of the formula P3.1 above.

2. The process of claim 1, wherein the process further comprises the following steps:

(a) reacting a compound of formula 1:

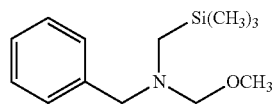

with a compound of the following formula:

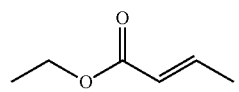

in the presence of trifluoroacetic acid (TFA), to provide a compound of formula Rac-2:

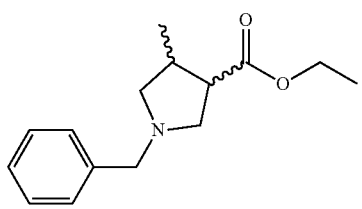

(b) reacting the compound of formula Rac-2 above with (+)-O,O-dibenzoyl-D-tartaric acid, to provide a compound of formula (S,S)-2:

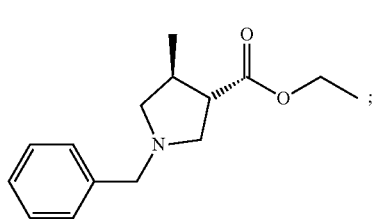

(c) reacting the compound of formula (S,S)-2 above with di(tert-butyl) dicarbonate, followed by reacting with hydrogen gas in the presence of a Pd/C catalyst, to provide a compound of formula (S,S)-3:

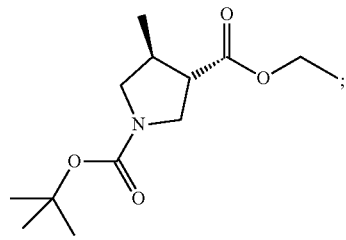

and (d) reacting the compound of formula (S,S)-3 above with a compound of the following formula:

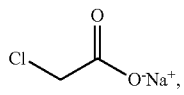

in the presence of triethylamine and tert-butyl magnesium chloride, to provide a compound of formula (S,S)-4:

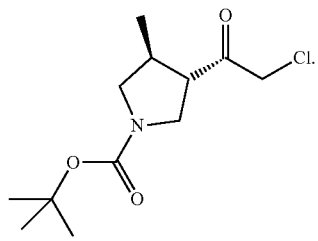

(S,S)-4

3. The process of claim 2, wherein the chiral purity of the compound of formula (S,S)-2 is in the range of 99.89%-99.98%.

4. The process of claim 1, wherein the process further comprises the following steps:

(a) reacting a compound of formula 5:

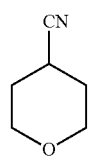

5 with diisobutylaluminum hydride (DIBAL-H), to provide a compound of formula 6:

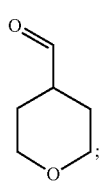

6

(b) reacting the compound of formula 6 above with a compound of the following formula:

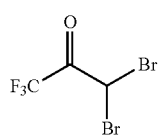

in the presence of aqueous ammonia, to provide a compound of formula 7:

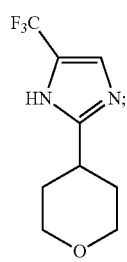

7

(c) reacting the compound of formula 7 above with sodium methoxide (NaOMe), to provide a compound of formula 8:

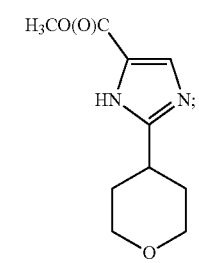

8 and (d) reacting the compound of formula 8 above with N-bromosuccinimide (NBS), to provide a compound of formula 9:

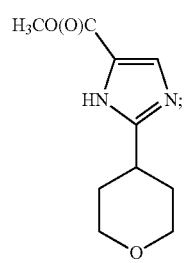

9

5. The process of claim 1, wherein step (a) is performed in a single reactor.

6. The process of claim 1, wherein the chiral purity of 6-((3S,4S)-4-methyl-1-(pyrimidin-2-ylmethyl)pyrrolidin-3-yl)-3-tetrahydropyran-4-yl-7H-imidazo[1,5-a]pyrazin-8-one of formula P3.1 is in the range of 95.0%-99.9%.

7. The process of claim 1, wherein the purity of 6-((3S, 4S)-4-methyl-1-(pyrimidin-2-ylmethyl)pyrrolidin-3-yl)-3-tetrahydropyran-4-yl-7H-imidazo[1,5-a]pyrazin-8-one of formula P3.1 is in the range of 95.0%-99.9%.

8. The process of claim 1, wherein the total amount of all impurities is in the range of 0.1%-5%.

9. The process of claim 1, wherein the yield of 6-((3S, 4S)-4-methyl-1-(pyrimidin-2-ylmethyl)pyrrolidin-3-yl)-3-tetrahydropyran-4-yl-7H-imidazo[1,5-a]pyrazin-8-one of formula P3.1 is in the range of 50%-80%.

* * * * *